United States Patent
Chantalat et al.

(10) Patent No.: US 10,232,006 B2
(45) Date of Patent: *Mar. 19, 2019

(54) PHARMACEUTICAL COMPOSITION COMPRISING REFINED INDIGO NATURALIS EXTRACT AND THE USE THEREOF

(71) Applicant: Galderma S.A., Cham (CH)

(72) Inventors: Laurent Chantalat, Antibes (FR); Philippe Andres, Peymeinade (FR)

(73) Assignee: Galderma S.A., Cham (CH)

(*) Notice: Subject to any disclaimer, the term of this patent is extended or adjusted under 35 U.S.C. 154(b) by 10 days.

This patent is subject to a terminal disclaimer.

(21) Appl. No.: 15/592,911

(22) Filed: May 11, 2017

(65) Prior Publication Data
US 2017/0304381 A1 Oct. 26, 2017

Related U.S. Application Data

(63) Continuation of application No. PCT/EP2016/057763, filed on Apr. 8, 2016.

(30) Foreign Application Priority Data

Apr. 9, 2015 (EP) .................................... 15163061

(51) Int. Cl.
*A61K 36/70* (2006.01)
*A61K 36/19* (2006.01)
(Continued)

(52) U.S. Cl.
CPC .............. *A61K 36/70* (2013.01); *A61K 8/492* (2013.01); *A61K 8/4953* (2013.01); *A61K 8/97* (2013.01);
(Continued)

(58) Field of Classification Search
None
See application file for complete search history.

(56) References Cited

U.S. PATENT DOCUMENTS

2003/0054047 A1* 3/2003 Zhao ................... A61K 36/19
424/725
2010/0034757 A1 2/2010 Fujii et al.
(Continued)

FOREIGN PATENT DOCUMENTS

CN 1317322 A 10/2001
CN 1316996 C * 5/2007
(Continued)

OTHER PUBLICATIONS

Tang W., Eisenbrand G., Qingdai. In: Chinese Drugs of Plant Origin. Springer, Berlin, Heidelberg pp. 805-806 (Year: 1992).*
(Continued)

*Primary Examiner* — Robert A Wax
*Assistant Examiner* — Melissa S Mercier
(74) *Attorney, Agent, or Firm* — Panitch Schwarze Belisario & Nadel LLP

(57) ABSTRACT

A refined Indigo Naturalis extract or Indigo-producing plant extract containing at least 65% (w/w) an indirubin derivative based on total weight of active ingredients is described. Also described are a pharmaceutical composition containing the refined extract, and the use of the pharmaceutical composition for treating or alleviating a disease or condition.

20 Claims, 8 Drawing Sheets

(51) Int. Cl.

| | |
|---|---|
| *A61K 36/315* | (2006.01) |
| *A61K 36/48* | (2006.01) |
| *A61K 8/49* | (2006.01) |
| *A61K 8/97* | (2017.01) |
| *A61K 9/00* | (2006.01) |
| *A61K 9/06* | (2006.01) |
| *A61K 31/404* | (2006.01) |
| *A61K 31/519* | (2006.01) |
| *A61Q 19/08* | (2006.01) |

(52) U.S. Cl.
CPC ......... *A61K 9/0014* (2013.01); *A61K 9/0053* (2013.01); *A61K 9/06* (2013.01); *A61K 31/404* (2013.01); *A61K 31/519* (2013.01); *A61K 36/19* (2013.01); *A61K 36/315* (2013.01); *A61K 36/48* (2013.01); *A61Q 19/08* (2013.01); *A61K 2236/00* (2013.01); *A61K 2800/92* (2013.01)

(56) References Cited

U.S. PATENT DOCUMENTS

| | | |
|---|---|---|
| 2012/0213868 A1 | 8/2012 | Lin |
| 2013/0331400 A1 | 12/2013 | Kusakari et al. |
| 2014/0243354 A1 | 8/2014 | Chantalat et al. |

FOREIGN PATENT DOCUMENTS

| | | | | |
|---|---|---|---|---|
| CN | 102351863 A | * | 2/2012 | |
| CN | 103766415 A | | 5/2014 | |
| CN | 103992260 A | * | 8/2014 | |
| EP | 0987027 A1 | | 3/2000 | |
| EP | 1495762 A1 | | 1/2005 | |
| EP | 1495764 A1 | | 1/2005 | |
| EP | 2489358 A1 | | 8/2012 | |
| JP | 2003002989 | * | 5/2002 | ............ A61K 35/78 |
| JP | 2006-241080 A | | 9/2006 | |
| KR | 20050077310 A | | 8/2005 | |
| KR | 2013-0071857 A | | 7/2013 | |
| WO | WO-0061159 A1 | * | 10/2000 | ............ A61K 31/519 |
| WO | 2005076757 A2 | | 8/2005 | |
| WO | 2014118040 A1 | | 8/2014 | |

OTHER PUBLICATIONS

CN 103992260A, google translation (Year: 2018).*
CN 1316996C, google translation (Year: 2018).*
CN102351863A, google translation (Year: 2018).*
WO0061159, google translation (Year: 2018).*
Tang et al. Chinese Drugs of Plant Origin, pp. 805-812 (1992). (Year: 1992).*
Int'l Search Report and Written Opinion dated Jun. 20, 2016 in Int'l Application No. PCT/EP2016/057763.
Int'l Search Report and Written Opinion dated Jun. 21, 2016 in Int'l Application No. PCT/EP2016/057769.
Chiang, "An in Vitro Study of the Antimicrobial Effects of Indigo Naturalis Prepared from Strobilanthes Formosanus Moore", Molecules, vol. 18, No. 11, pp. 14381-14396 (Nov. 21, 2013).
Han et al., "Genuine traditional Korean medicine, Naju Jjok (Chung-Dae Polygonum tinctorium) improves 2,4-dinitrofluorobenzene-induced atopic dermatitis-like lesional skin," Phytomedicine, vol. 24, pp. 453-460 (2014).
Han et al, "Tryptanthrin ameliorates atopic dermatitis through down-regulation of TSLP," Archives of Biochemistry and Biophysics, vol. 542, pp. 14-20 (2013).
Int'l Search Report and Written Opinion dated Jun. 20, 2016 in Int'l Application No. PCT/EP2016/057761.
Yang et al, "The Synergistic Activity of Antibodies Combined With Eight Traditional Chinese Medicines Against Two Different Strains of *Staphylococcus aureus*," Colloids and SurfacesB: Biointerfaces, vol. 41, pp. 79-81 (2005).
Shahni et al, "Antibacterial Properties of Leaf Extracts of Strobilanthes Cusia (Nees) Kuntze, A Rare Ethno-Medicinal Plant of Manipur, India," International Journal of PharmTech Research, vol. 5, No. 3, pp. 1281-1285 (2013).
Ravichandran et al, "Phytochemical Screening and In-Vitro Antibacterial Activity of Leaf Extracts of Indigofera Tinctoria Linn," International Journal of Advances in Pharmaceutical Research, vol. 3, Issue 4, pp. 872-877 (2012).
Ponnusamy et al, "Indirubin Potentiates Ciprofloxacin Activity in the NorA Efflux Pump of *Staphylococcus aureus*," Scandinavian Journal of Infectious Diseases, vol. 42, pp. 500-505 (2010).
Thangadurai et al, "Indigoferabietone, A Novel Abietane Diterpenoid From Indigofera Iongeracemosa With Potential Antituberculous and Antibacterial Activity," Pharmazie, vol. 57, pp. 714-715 (2002).
Int'l Search Report dated Jun. 21, 2016 in Int'l Application No. PCT/EP2016/057775.
Wang et al., "Effects of indigo naturalis on colonic mucosal injuries and inflammation in rats with dextran sodium sulphate-induced ulcerative colitis" Experimental and Therapeutic Medicine, 14, pp. 1327-1336, 2017.

* cited by examiner

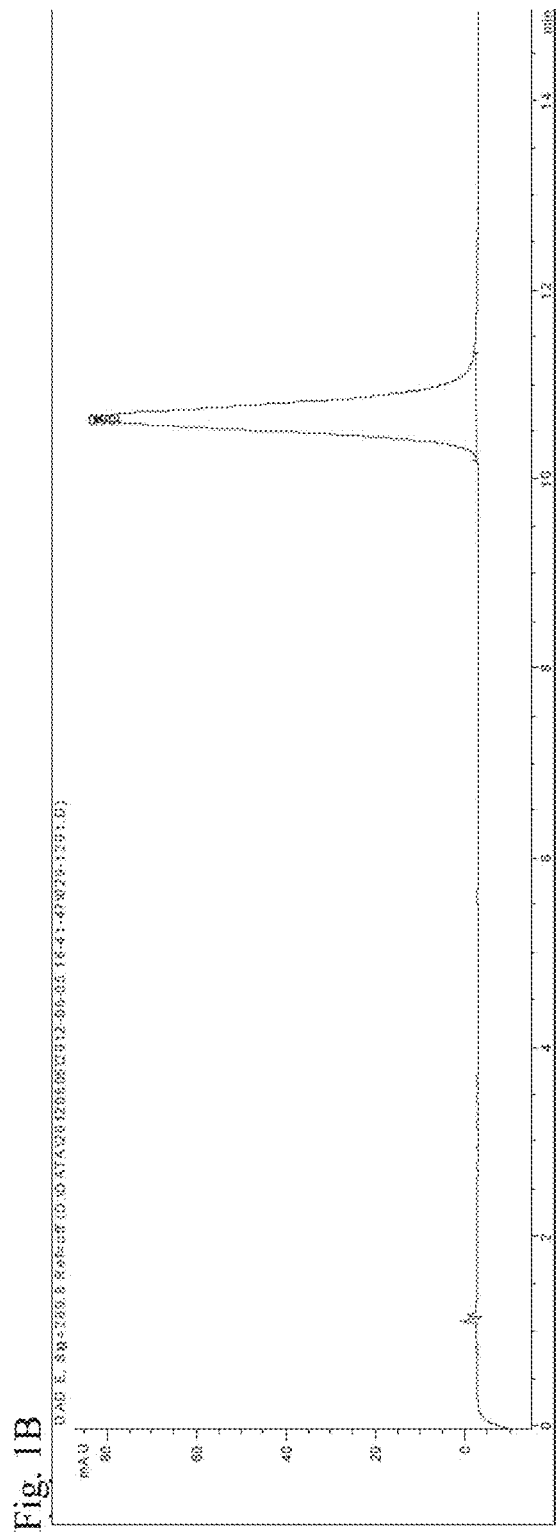

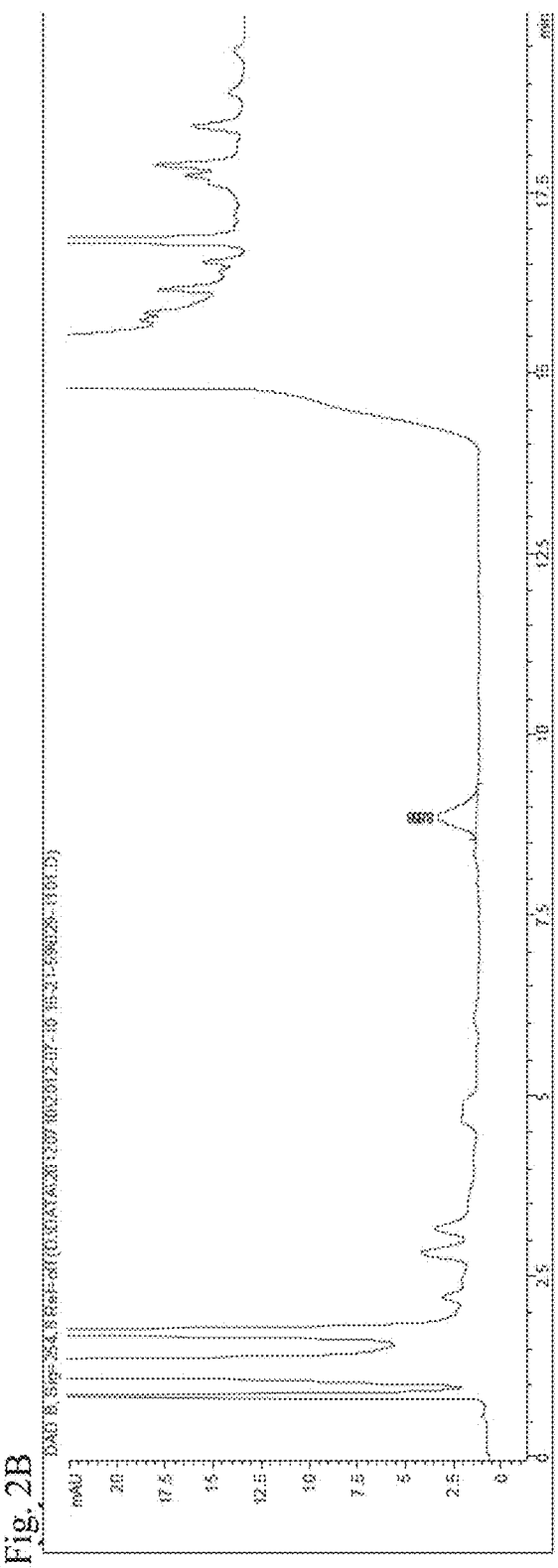

Fig. 3A STUDY 1
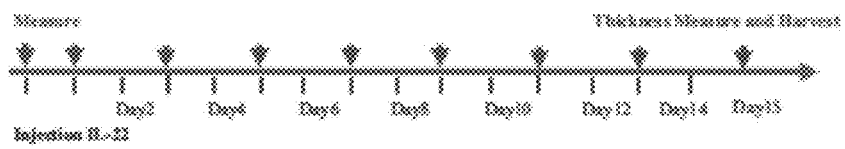
Fig. 3B STUDY 2
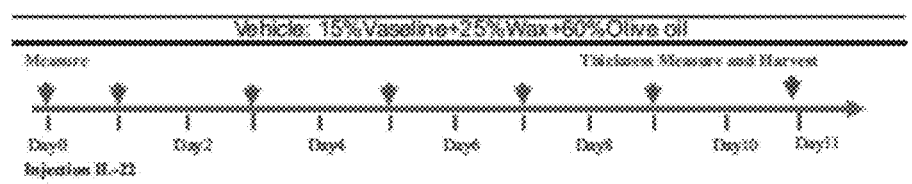
Fig. 3C STUDY 3
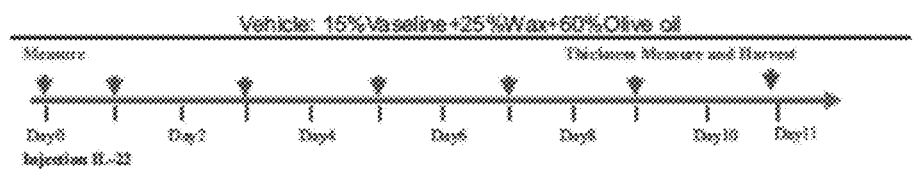
Fig. 3D STUDY 4
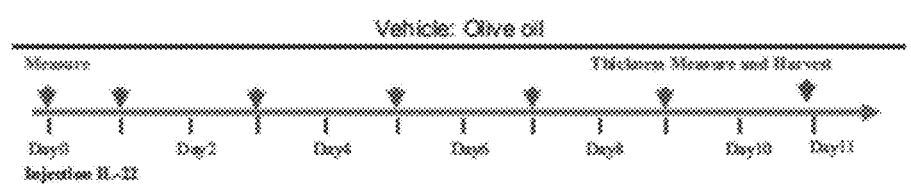
Fig. 3E STUDY 5
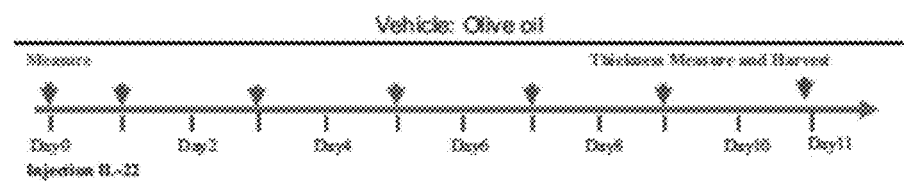

PHARMACEUTICAL COMPOSITION COMPRISING REFINED INDIGO NATURALIS EXTRACT AND THE USE THEREOF

CROSS-REFERENCE TO RELATED APPLICATION

This application claims the benefit, under 35 U.S.C. § 365 of International Application PCT/EP2016/057763 filed Apr. 8, 2016, which was published in the English language on Oct. 13, 2016, under International Publication No. WO 2016162485A1, and which claims the benefit of European patent application No. 15163061.3, filed Apr. 9, 2015, the disclosure of each of which is hereby incorporated by reference herein in its entirety.

TECHNICAL FIELD

The present invention relates to a pharmaceutical composition, as well as the use of composition in medical applications.

BACKGROUND

The conventional treatments for psoriasis are generally designed according to the age, gender, occupation and cognitive ability of a patient, the types and distribution of lesions, patient's response(s) to previous therapeutic method(s), and other medical histories of the patient. The primary therapeutic methods for psoriasis include topical therapy, systemic therapy, injection of biologics and phototherapy. Compositions for topical therapy include, e.g., corticosteroids, anthralin (available as Margiton®), coal tar (available as Polytar®), calcitriol (available as Silkis®), tazarotene (available as Tazorac®), salicylic acid, and these compositions are suitable for treating psoriasis patients with mild symptoms. Oral preparations of e.g., methotrexate (MTX), cyclosporine, and retinoids are commonly used for systemic therapy and are suitable for treating psoriasis patients with medium to severe symptoms. Biologics include alefacept (available as Amevive®), efalizumab (available as Raptiva®), etanercept (available as Enbrel®) and adalimumab (available as Humira®), and they are suited for injecting into psoriasis patients with medium to severe symptoms. Phototherapy, e.g., ultraviolet B (UVB) phototherapy, photochemotherapy such as psoralen plus ultraviolet A (PUVA), is suitable for treating psoriasis patients with severe symptoms.

However, additional therapeutic methods are desirable.

SUMMARY

The present invention, in part, relates to a pharmaceutical composition including at least 65% (w/w) an indirubin derivative based on total weight of active ingredients.

The active ingredients according to the present invention refer to ingredients including one or more of indirubin derivatives, indigo derivatives, tryptanthrin derivatives, isatin derivatives and qingdainone derivatives, or to a plant extract (e.g., an Indigo Naturalis extract or refined extract of Indigo Naturalis) containing one or more of indirubin derivatives, indigo derivatives, tryptanthrin derivatives, isatin derivatives and qingdainone derivatives.

In one aspect, the present invention provides a pharmaceutical composition with at least 65% (w/w) an indirubin derivative based on total weight of active ingredients (for example, at least 70%, 75%, 80% or 85% (w/w) based on total weight of active ingredients), and a pharmaceutically acceptable carrier.

In some embodiments, the composition comprises 65-90% (w/w) of an indirubin derivative and 0-15% of an indigo derivative based on total weight of active ingredients and a pharmaceutically acceptable carrier. For example, the indirubin derivative, including one or more indirubin derivatives, can be in an amount of 65-90% (w/w), e.g., 65-70%, 65-75%, 65-80%, 65-85%, 65-90%, 70-75%, 70-80%, 70-85%, 70-90%, 75-80%, 75-85%, 75-90%, 80-85%, 80-90%, or 85-90% (w/w) based on total weight of active ingredients. The indigo derivative, including one or more indigo derivatives, can be in an amount of 0-15%, e.g., 0.05-15%, 0.1-15%, 0.5-15% (w/w) based on total weight of active ingredients.

In some examples, an indirubin derivative, including one or more indirubin derivatives, can be in an amount of 20-500 ppm based on the pharmaceutical composition, e.g., 20-100 ppm, 20-200 ppm, 20-300 ppm, 20-400 ppm, 20-500 ppm, 50-100 ppm, 50-200 ppm, 50-300 ppm, 50-400 ppm, 50-500 ppm, 100-200 ppm, 100-300 ppm, 100-400 ppm, 100-500 ppm, 200-300 ppm, 200-400 ppm, 200-500 ppm, 300-400 ppm, 300-500 ppm or 400-500 ppm.

In some other examples, an indigo derivative, including one or more indigo derivatives, can be in an amount of 0.1-40 ppm based on the pharmaceutical composition, e.g., 0.15 ppm, 0.1-10 ppm, 0.1-20 ppm, 0.1-30 ppm, 0.1-40 ppm, 1-5 ppm, 1-10 ppm, 1-20 ppm 1-30 ppm, 1-40 ppm, 5-10 ppm, 5-20 ppm, 5-30 ppm, 5-40 ppm, 10-20 ppm, 10-30 ppm, 10-40 ppm, 20-30 ppm, 20-40 ppm or 30-40 ppm.

In some other embodiments, the composition further comprises a tryptanthrin derivative. The tryptanthrin derivative, including one or more tryptanthrin derivatives, can be in an amount of 0.01-5% (w/w), preferably 0.1-5% (w/w) based on the total weight of active ingredients, e.g., 0.1-1%, 0.1-5%, 0.5-1%, or 0.5-5% (w/w) based on the total weight of active ingredients.

In some examples, a tryptanthrin derivative, including one or more tryptanthrin derivatives, can be in an amount of 0.1-10 ppm based on the pharmaceutical composition, e.g., 0.1-1 ppm, 0.1-5 ppm, 0.1-10 ppm, 1-5 ppm, 1-10 ppm, or 5-10 ppm.

In further some embodiments, the composition further comprises a qingdainone derivative as a component. The qingdainone derivative, including one or more qingdainone derivatives, can be in an amount of 0.1-5% (w/w) based on the total weight of active ingredients, e.g., 0.1-1%, 0.1-3%, 0.5-1%, or 0.5-5% (w/w) based on active ingredients.

In some examples, a qingdainone derivative, including one or more qingdainone derivatives, can be in an amount of 0.1-10 ppm based on the pharmaceutical composition, e.g., 0.1-1 ppm, 0.1-5 ppm, 0.1-10 ppm, 1-5 ppm, 1-10 ppm, or 5-10 ppm.

In further some embodiments, the composition further comprises an isatin derivative as a component. The isatin derivative, including one or more isatin derivatives, can be in an amount of 0.1-5% (w/w) based on active ingredients.

In some examples, an isatin derivative, including one or more isatin derivatives, can be in an amount of 0.1-10 ppm based on the pharmaceutical composition, e.g., 0.1-1 ppm, 0.1-5 ppm, 0.1-10 ppm, 1-5 ppm, 1-10 ppm, or 5-10 ppm.

In a further embodiment, the pharmaceutical composition comprises:
from 0.002% to 0.077% (w/w) of a refined extract of Indigo Naturalis, and
a pharmaceutically acceptable carrier,
wherein the refined extract of Indigo Naturalis comprises from 65% to 90% (w/w) of indirubin and one or more of derivatives selected from the list consisting of indigo, tryptanthrin and qingdainone with the following amount:
indigo: 0.1 to 15% (w/w) of the refined extract,
tryptanthrin: 0.01 to 5%, preferably 0.1 to 5% (w/w) of the refined extract, and
qingdainone: 0.1 to 5% (w/w) of the refined extract.

In a particular embodiment, the composition of the invention is in the form for topical administration or oral administration.

In another aspect, the present invention provides an afore-described composition for use in the treatment or alleviation of a disease or condition selected from the group consisting of psoriasis, inflammatory skin conditions, onychomycosis, skin cancer, abnormal keratinization induced diseases, skin aging, pustular dermatosis.

In another aspect, the present invention provides a method for inhibiting proliferation or differentiation of keratinocytes, inhibiting infiltration of mononuclear cells into the dermis and epidermis, inhibiting vascular alteration resulting in hyperlastic blood vessels, or inhibiting upregulation of adhesion molecules on endothelia cells comprising contacting the just-described composition to a cell in need thereof. The method may be used in vivo or in vitro.

In still another aspect, the present invention provides use of an afore-described composition in the preparation of a product for the treatment or alleviation of a disease or condition selected from the group consisting of psoriasis, inflammatory skin conditions, onychomycosis, skin cancer, abnormal keratinization induced diseases, skin aging, pustular dermatosis and Cutaneous T Cell Lymphoma (CTCL).

In still further another aspect, the present invention provides a method for the treatment of skin disease or condition comprising administering an effective amount of an afore-described composition to a subject (e.g., human) in need thereof. The disease or condition is selected from the group consisting of psoriasis, inflammatory skin conditions, onychomycosis, skin cancer, abnormal keratinization induced diseases, skin aging, pustular dermatosis and CTCL. In some embodiments, the inflammatory skin conditions can be atopic dermatitis (AD), eczema or superinfected skin. The skin aging can be skin rejuvenation, tissue regeneration for scars or skin senescence. The abnormal keratinization can be acne, ichtyosis or palmoplantar keratoderma. The skin cancer can be precancerous skin cancer, for example, Actinic Keratosis (AK), bowen's disease; skin cancer, for example, SCC, BCC, NMSC; melanoma and HPV induced skin cancer.

DESCRIPTION OF DRAWINGS

The above and other features and advantages of the present invention will become apparent with reference to the following detailed description and the accompanying drawings.

FIGS. 1A, 1B: Illustrative HPLC chromatograms of indigo (FIG. 1A) and indirubin (FIG. 1B).

FIGS. 2A, 2B, 2C: Illustrative HPLC chromatograms of thryptanthrin (FIG. 2A), Qingdai (FIG. 2B) and a refined extract of example 2 (FIG. 2C).

FIGS. 3A, 3B, 3C, 3D, 3E: Group and dosing for in vivo evaluation of extracts from Qingdai in IL-22 induced psoriasis model. Five studies were designed and outlined in study 1-5, respectively. In Study 1, 100 ng and 500 ng of IL-22 in 20 µL, i.d., were used for induction. In study 2-5, 500 ng of IL-22 in 20 µL saline, i.d., were used for induction.

FIGS. 4A and 4B illustrate ear inflammation after intradermal injection of IL-22. In the studies, ears of mice were injected intradermally and ear thickness was measured on days between injections.

FIGS. 5A and 5B illustrate the effects of Indigo Naturalis extracts on ear inflammation after intradermal injection of IL-22.

DETAILED DESCRIPTION

Figure 1A:
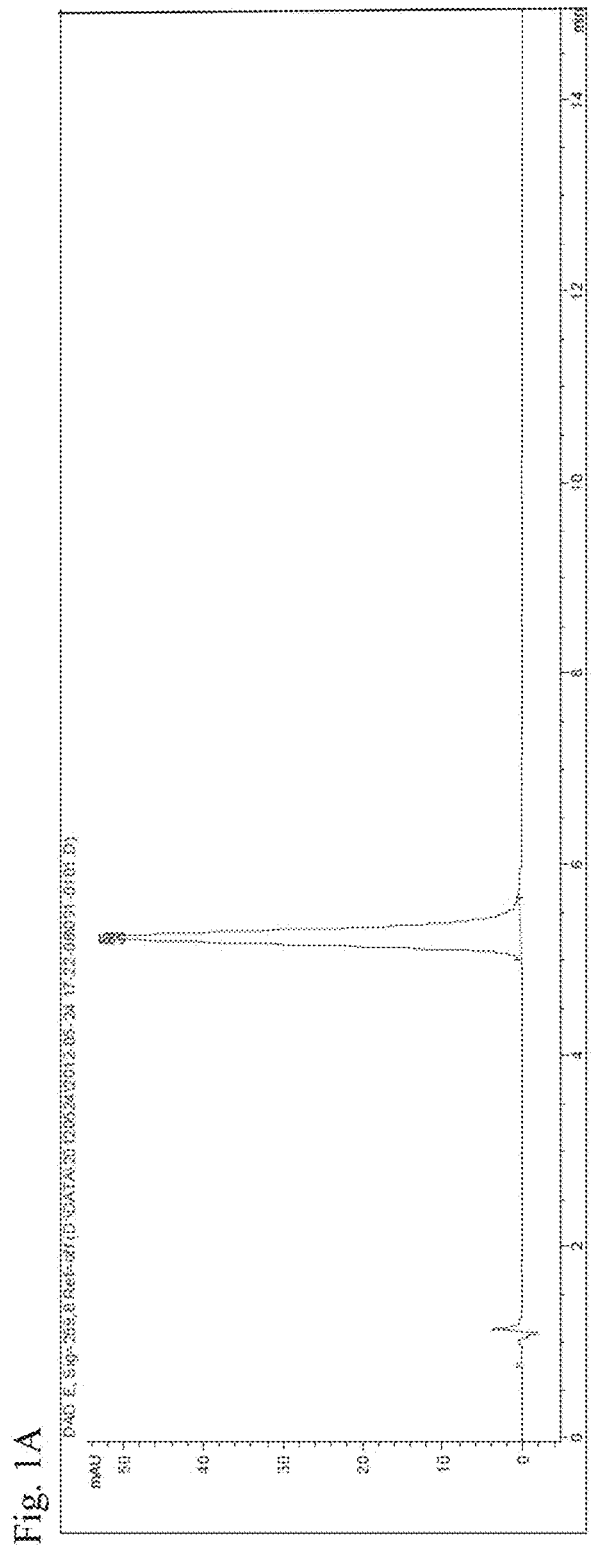

Indigo Naturalis, for example Qingdai, is a dark-blue powder prepared from leaves of Indigo-bearing plants or indigo-producing plants. Said plants are preferably selected from the group consisting of *Indigofera tinctoria* L., *Baphicacanthus cusia* (Nees) Bremek (syn. *Strobilanthes cusia* (Nees), *Persicaria tinctoria* (Alton) Spach. (syn. *Polygonum tinctorium Aiton, P. tinctorium* Lour.) and *Isatis tinctoria* L. (syn. *Isatis indigotica* Fort.).

Qingdai is the current name for *indigo Naturalis*, it is extracted from Indigo-bearing or Indigo-producing plants with a NaOH or KOH aqueous solution and corresponds to a mixture of around 5-15% organic compounds including alkaloids among which indigo and indirubin are present, and 85-95% inorganic compounds such as calcium carbonate and calcium hydroxide.

As used herein, indirubin, indigo, tryptanthrin, isatin and qingdainone have the following structures.

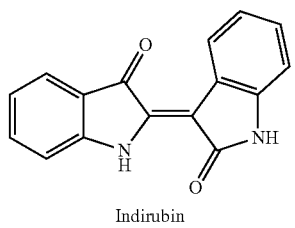

Indirubin

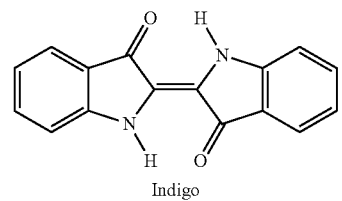

Indigo

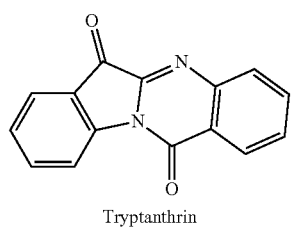

Tryptanthrin

-continued

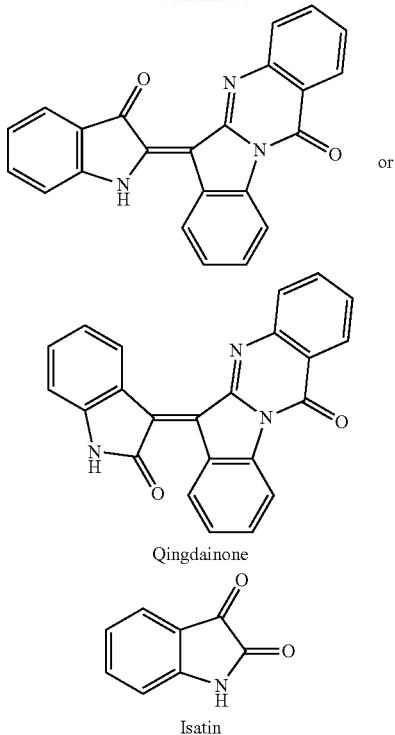
Qingdainone

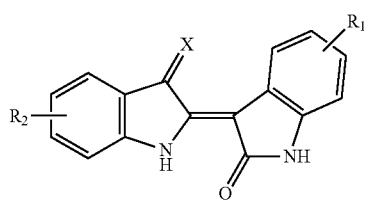
Isatin

An indirubin derivative, as used herein, refers to indirubin as well as a derivative thereof, for example represented by formula I formula I
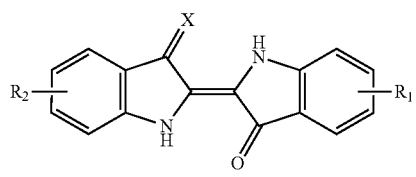

wherein, X is a heteroatom selected from any of N, O, and S; in a case of X=N, N is linked to a hydroxyl, or an alkyl substituted with hydroxyl, halogen or $NH_2$; $R_1$ and $R_2$ are one or more substituents selected from hydrogen, alkyl, OH, halogen, $NH_2$, $SO_3H$, $NO_2$; and the aforesaid alkyl is, for example, an alkyl having one to six carbon atoms.

An indigo derivative, as used herein, refers to indigo as well as a derivative thereof, for example represented by formula II formula II $X$, $R_1$ and $R_2$ are defined as those in formula I.

Examples of indigo derivatives and indirubin derivatives are as follows:

N-methylisoindigotin (meisoindigo);
N-acetyl-indirubin; and
Compounds represented as the following:

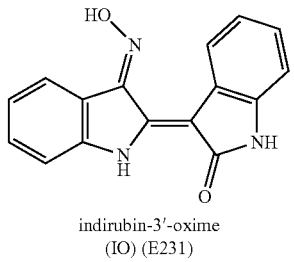
indirubin-3'-oxime
(IO) (E231)

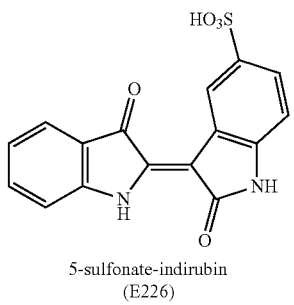
5-sulfonate-indirubin
(E226)

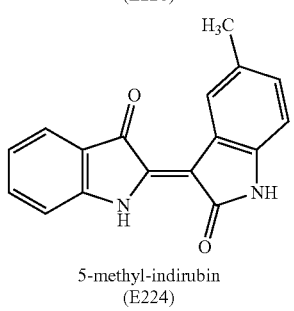
5-methyl-indirubin
(E224)

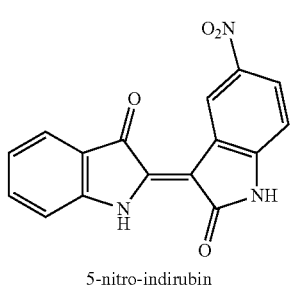
5-nitro-indirubin

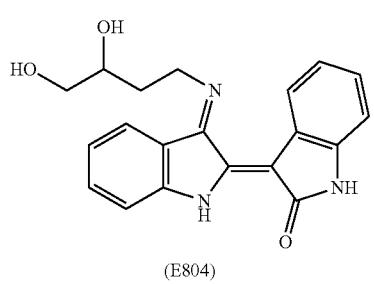
(E804)

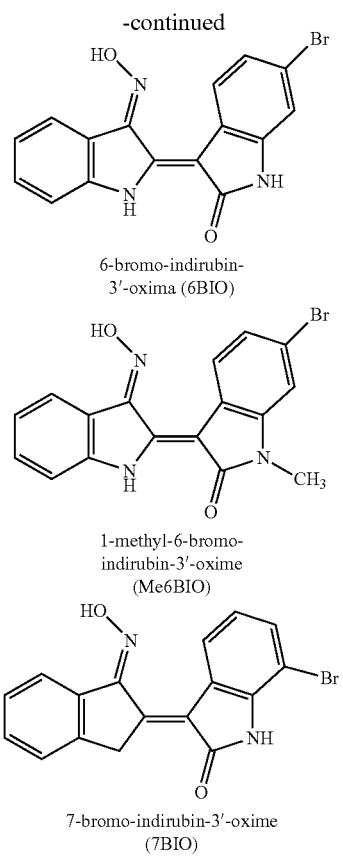

6-bromo-indirubin-3'-oxima (6BIO)

1-methyl-6-bromo-indirubin-3'-oxime (Me6BIO)

7-bromo-indirubin-3'-oxime (7BIO)

A tryptanthrin derivative, as used herein, refers to tryptanthrin as well as a derivative thereof. A derivative of tryptanthrin refers to a compound containing the tryptanthrin core, i.e., quinazoline ring fused to an indole moiety. One examples of a derivative of tryptanthrin is Phaitanthrin A, B, C, D or E; Methylisatoid, or Orphiuroidin, as depicted in Ashli M. Tucker and Peter Grundt, The chemistry of tryptanthrin and its derivatives, ARKIVOC 2012 (i) 546-569.

An isatin derivative, as used herein, refers to isatin and a derivative thereof. A derivative of isatin refers to a compound obtained from isatin, for example, those disclosed in Yun Mi Chung et al., Synthesis of ortho-Acetamidomandelic Acid Derivatives from Isatins, *Bull. Korean Chem. Soc.* 2002, Vol. 23, No. 10 1363; Ankur Patel et al., Synthesis and Antimicrobial Activity of Some New Isatin Derivatives, Iranian Journal of Pharmaceutical Research (2006) 4: 249-254; or Olcay Bekircan et al., Synthesis of Schiff and Mannich Bases of Isatin Derivatives with 4-Amino-4,5-Dihydro-1H-1,2,4-Triazole-5-Ones, *Molecules* 2008, 13, 2126-2135.

A qingdainone derivative refers to qingdainone itself as well as a derivative thereof. A derivative of qingdainone refers to a compound obtained from quindainone.

The term "an effective amount" refers to a dose level of the pharmaceutical composition yields a therapeutic benefit (for example, amelioration, alleviation or cure of the diseases, disorders or symptoms) to a patient on average.

The active ingredients described above can be chemically synthesized by methods known to one skilled in the art, or extracted from an Indigo-bearing plant, for example an Indigo Naturalis extract.

A process for preparing a refined extract from Qingdai is described below.

Indigo Naturalis is obtained from leaves and stems of Indigo bearing plant or indigo-producing plant, preferably selected from the group consisting of *Indigofera tinctoria* L., *Baphicacanthus cusia* (Nees) Bremek (syn. *Strobilanthes cusia* (Nees), *Persicaria tinctoria* (Aiton) Spach. (syn. *Polygonum tinctorium* Aiton, *P. tinctorium* Lour.) and *Isatis tinctoria* L. (syn. *Isatis indigotica* Fort.). While Indigo Naturalis or Qingdai is commercially available (examples of Indigo Naturalis commercially available (plant/supplier): *Baphicacanthus cusia*/Delong; Indigoferatinctoria/KMA exports or SAM VEGETABLE COLOURS PVT LTD or SICHUAN XIELI; *Isatis tinctoria*/ANDREA PRIMAVERA or Bleu de Lectoure; *Polygonum tinctorium*/Couleur Garance or EARL 4 saisons), it can be produced from the leaves and/or stems of one or more of above plants by methods commonly known in the art. These methods can be summarized as follows: freshly harvested stems and leaves of *Persicaria Tinctoria* and/or *Baphicacanthus cusia* are added to a pool in the open air, the water is added to the pool to cover the stems/leaves. After soaking for few days (26-30° C.), the stems/leaves will become rotten. Then lime soda is added while stirring. When the color of the soaking mixture changed from green to deep violet, the precipitate is collected, washed (usually with water for 2-3 times), and then dried to yield Indigo Naturalis powder.

A refined extract may be prepared by a process comprising:
a) an extraction step: extracting Indigo Naturalis or the leaves and/or stems of one or more plants as selected above with a first polar solvent or moderately polar solvent to obtain a mixture of extraction;
b) a filtration step: filtering the mixture of extraction to obtain a filtrate;
c) a concentration step: concentrating the filtrate to obtain a crude extract;
d) a washing step: washing the crude extract with a non-polar solvent, and optionally a second polar solvent, to obtain a washing mixture; and
e) a filtration step: filtering the washing mixture to obtain a refined extract optionally after a drying step, for example, according to a conventional method for drying.

In a particular embodiment, a crude extract obtained from the concentration step c) is subjected to the following procedure for at least one cycle till obtaining a refined extract: the crude extract is washed by a solvent (step d)), and filtered (step (e)) to yield a refined extract, optionally followed by a drying step. According to a specific embodiment, the washing step d) and filtration step e) are performed by only one cycle to obtain the refined extract. When more than one cycle is applied, the same or different solvents for washing can be used. Further, the crude extract can be washed with a solvent under reflux, the mixture can be cooled to room temperature and then filtered to yield a refined extract, optionally followed by a drying step.

In a preferred embodiment, two cycles are performed. Particularly, the crude extract obtained by the concentration step c) is washed in a non-polar solvent, preferably hexane (step d) and filtered (step e), optionally followed by a drying step. The hexane extract is then washed by an organic polar solvent, preferably ethanol (step d) and then filtered (step e) to obtain a refined extract, optionally followed by a drying step.

Optionally, a micronization step is performed after step e), providing thereby a refined extract having a particle size between 25 and 35 μm, preferably of about 30 μm.

In a preferred embodiment, a refined extract may be prepared by a process comprising the following steps consisting of: a) (i) adding an extracting solvent, a polar or moderately polar solvent (such as an alcohol or ethyl acetate), to Indigo Naturalis powder to yield a mixture; (ii) heating and stirring the mixture for a period of time (e.g., 30 min, 1 hour, 2 hours); b) (iii) filtering the heated mixture while hot to remove insoluble by-products to yield a filtrate; c) (iv) concentrating the filtrate to yield a crude extract; d) (v) adding a washing solvent (for example, water a non-polar and/or a polar solvent or a mixture thereof) to the crude extract to yield a washing mixture; (vi) heating and stirring the washing mixture for a period of time (e.g., 30 min, 1 hour, 2 hours); e) (vii) filtering the washing mixture, for example at room temperature (e.g. 18-35° C.) to collect a refined extract; optionally (viii) repeating steps (v) to (vii) until the amount of indirubin (% w/w) in the refined extract is more than 55% (w/w), preferably more than 65% (w/w) as measured by HPLC method disclosed in Example 8A, and optionally (ix) drying the residue according to a conventional method (e.g., air-drying, lyophilization) to obtain a dried extract. The washing solvent in steps (v) and (viii) can be the same or different.

In a more preferred embodiment, a refined extract is prepared by a process comprising the steps of:
a) extracting Indigo Naturalis with ethanol at reflux between 2 and 8 hours,
b) filtering the mixture at a temperature not less than 65° C. to obtain a filtrate,
c) concentrating the filtrate, to obtain a crude extract, said crude extract is optionally filtered (with addition of water) in order to remove completely the solvent and the last components still present in the solvent and dried,
d) (i) washing the crude extract with hexane at a temperature not less than 50° C. between 15 and 60 min,
(ii) filtering at room temperature the mixture obtained at step d) (i) to obtain a product, optionally rinsing it with ethanol and water
(iii) washing the product obtained at step d) (ii) with ethanol at reflux, and
e) filtering at room temperature the washing mixture obtained at step d) and drying the resulting product at a temperature less than 80° C. to obtain an extract which is optionally micronized.

In another preferred embodiment, when the refined extract is micronized in the last step, the particle size is in the range 25 to 35 μm, preferably of about 30 μm.

In another preferred embodiment, when the refined extract is micronized in the last step, 99% of the obtained particles are less or equal to 30 μm.

As used herein, "about" or "around" will be understood by a person of ordinary skill in the art and will vary to some extent on the context in which it is used. If there are uses of the term which are not clear to persons of ordinary skill in the art given the context in which it is used, "about" or "around" will mean up to plus or minus 20%, preferably 10% of the particular term.

The term "refined extract", as used herein, refers to a solid, semi-solid or oily extract, preferably solid extract, which contains less than 10% (w/w) of water and/or solvents used in the process for preparing the said refined extract. A refined extract is more preferably characterized by an increase amount of active ingredients, including alkaloids among which indigo, indirubin, tryptanthrin, and/or qingdainone are present, preferably enriched in indirubin, compared to Qingdai or Indigo Naturalis. More specifically, the refined extract according to the invention comprises at least 60%, or more preferably more than 65%, (w/w) of active ingredients, including indigo, indirubin, tryptanthrin, and/or qingdainone.

The term "crude extract", as used herein, refers to a solid, semi-solid or oily extract, preferably solid or semi-solid extract, which contains less than 15% (w/w) (e.g., 5-15%, 5-10%) of water and/or solvents used in the process for preparing the refined extract. The crude extract is less enriched in indirubin, than the refined extract as compared to Qingdai or Indigo Naturalis. The crude extract is obtained by the concentration step c) according to the invention. The concentration step is more particularly carried out by sending the filtrate to a concentrator (for instance at reduced pressure), as to remove water and/or solvents used in the process and concentrating thereby the active ingredients present in the extract, including indigo, indirubin, tryptanthrin, isatin and/or qingdainone derivatives.

"one cycle", as used herein, refers to the two steps of the washing step d) and filtration step e) which are performed sequentially once. "two cycles", as used herein, refers to the two steps of the washing step d) and filtration step e) which are performed sequentially twice.

The contents of ingredients such as indigo, indirubin, tryptanthrin and qingdainone can be quantitated by HPLC methods as disclosed in Example 8.

The afore-mentioned refined extract from Qingdai or a refined extract from the leaves and/or stems of an Indigo bearing plant or indigo-producing plants, preferentially selected from the group consisting of *Indigofera tinctoria* L., *Baphicacanthus cusia* (Nees) Bremek (syn. *Strobilanthes cusia* (Nees), *Persicaria tinctoria* (Aiton) Spach. (syn. *Polygonum tinctorium* Aiton, *P. tinctorium* Lour.) and *Isatis tinctoria* L. (syn. *Isatis indigotica* Fort.) includes indirubin as a component in an amount of at least 65% (w/w) of the refined extract. The extract is in a solid form and may be prepared by the process described above or any other suitable process. The extract may further include indigo, tryptanthrin, qingdainone, and/or any derivative of these compounds, which may be co-extracted together with indirubin. In particular, the extract containing multi-ingredients may provide a synergistic effect.

In the refined extract obtained by the above process, Indirubin derivative and at least one or more of indigo, tryptanthrin and qingdainone derivatives are present in the following amount:
Indigo derivative: from 0.1% to 15% (w/w) of the refined extract,
Indirubin derivative: from 65% to 90% (w/w) of the refined extract,
Tryptanthrin derivative: from 0.01 to 5% (w/w), preferably from 0.1% to 5% (w/w) of the refined extract,
Qingdainone derivative: from 0.1% to 5% (w/w) of the refined extract.

In a preferred embodiment, in the refined extract obtained by the above process, Indirubin and at least one or more of indigo, tryptanthrin and qingdainone are present in the following amount:
Indigo: from 0.1% to 15% (w/w) of the refined extract,
Indirubin: from 65% to 90% (w/w) of the refined extract,
tryptanthrin: from 0.01 to 5% (w/w), preferably from 0.1% to 5% (w/w) of the refined extract,
qingdainone: from 0.1% to 5% (w/w) of the refined extract.

The present invention further provides a pharmaceutical composition, which may be formulated into a suitable dosage form for topical or oral administration using technology well known to those skilled in the art. The pharmaceutical composition can additionally comprise a pharmaceutically acceptable carrier such as those widely employed in the art of drug-manufacturing. For instance, the pharmaceutically acceptable carrier may include one or more of the following agents: solvents such as olive oil, refined olive oil, cotton seed oil, sesame oil, sunflower seed oil, peanut oil, wheat germ oil, soybean oil, jojoba oil, evening primrose oil, coconut oil, palm oil, sweet almond oil, aloe oil, apricot kernel oil, avocado oil, borage oil, hemp seed oil, macadamia nut oil, rose hip oil, pecan oil, hazelnut oil, sasanqua oil, rice bran oil, shea butter, corn oil, camellia oil, grape seed oil, canola oil, castor oil, and combinations thereof, preferably olive oil refined, emulsifiers, suspending agents, decomposers, binding agents, excipients, stabilizing agents, chelating agents, diluents, gelling agents, thickening agent such as beeswax and/or petroleum jelly, preservatives, lubricants, absorption delaying agents, liposomes, antioxidants such as butylhydroxytoluene or butylhydroxyanisole, and the like. Preferably, the pharmaceutical composition is formulated into a topical formulation that can be directly applied to the skin, for example, a skin suffering from psoriasis. The topical formulation suitable for the pharmaceutical composition may be an emulsion, a gel, an ointment, a cream, a patch, an embrocation, an aerosol, a spray, a lotion, a serum, a paste, a foam, or a drop. In one embodiment of the present invention, the pharmaceutical composition is formulated into an external preparation by admixing the extract according to the present invention with a base such as those that are well known and commonly used in the art.

In some embodiments, a pharmaceutical composition, as disclosed above, can comprise from 0.002% to 0.077% (w/w) of a refined extract of Indigo Naturalis, and a pharmaceutically acceptable carrier, wherein, the refined extract of Indigo Naturalis comprises from 65% to 90% (w/w) of indirubin derivative and one or more of derivatives selected from the list consisting of indigo, thryptanthrin and qingdainone with the following amount:
    indigo derivative: 0.1 to 15% (w/w) of the refined extract,
    tryptanthrin derivative: 0.01 to 5% (w/w), preferably 0.1 to 5% (w/w) of the refined extract, and
    qingdainone derivative: 0.1 to 5% (w/w) of the refined extract.

In some preferred embodiments, a pharmaceutical composition, as disclosed above, can comprise from 0.002% to 0.077% (w/w) of a refined extract of Indigo Naturalis, and a pharmaceutically acceptable carrier, wherein, the refined extract of Indigo Naturalis comprises from 65% to 90% (w/w) of indirubin and one or more of derivatives selected from the list consisting of indigo, thryptanthrin and qingdainone with the following amount:
    indigo: 0.1 to 15% (w/w) of the refined extract,
    tryptanthrin: 0.01 to 5% (w/w), preferably 0.1 to 5% (w/w) of the refined extract, and
    qingdainone: 0.1 to 5% (w/w) of the refined extract.

In some embodiments, the dosage and the frequency of administration of the pharmaceutical composition according to the present invention may vary depending on the following factors: the severity of the disease to be treated, the route of administration, and the weight, age, physical condition and response of the subject to be treated. In further or additional embodiments, the amount of the active ingredients in the pharmaceutical composition is in the range of about 0.001 to about 1000 mg/kg body weight/day, for example, about 0.01 to about 500, 300, or 100 mg/kg body weight/day. I The compositions above can be used in the treatment or alleviation of a disease or condition. By treatment it is meant at least an alleviation of the symptoms associated with the pathological condition afflicting the subject, where alleviation is used in a broad sense to refer to at least a reduction in the magnitude of a parameter, e.g. symptom, associated with the pathological condition being treated, such as dermatitis, psoriasis and the like. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition. As such, treatment includes both curing and managing a disease condition. Accordingly, the compositions above can be used in the treatment or alleviation of a disease or condition selected from the group consisting of psoriasis, inflammatory skin conditions, onychomycosis, skin cancer, abnormal keratinization induced diseases, skin aging, and pustular dermatosis.

The present invention further provides a method for inhibiting proliferation or differentiation of keratinocytes, inhibiting infiltration of mononuclear cells into the dermis and epidermis, inhibiting vascular alteration resulting in hyperlastic blood vessels, or inhibiting upregulation of adhesion molecules on endothelia cells comprising administering the compositions above to a subject in need thereof.

The efficacy of the compositions can be evaluated by in vitro models with respect to their activities in inhibiting proliferation or differentiation, or inflammation. For example, in vitro testing can be conducted on cytokine signaling, STAT-3/STAT-1, MAPK, NFκB involved pathways.

The efficacy of the compositions can be further evaluated by in vivo models with respect to their activities in treating diseases or disorders. For example, genetically engineered mice, including the transgenic and knockout models, can be tested.

The novel features of the application are set forth with particularity in the appended claims. A better understanding of the features and advantages of the present application will be obtained by reference to the following detailed description that sets forth illustrative embodiments, in which the principles of the application are utilized.

While preferred embodiments of the present application have been shown and described herein such embodiments are provided by way of example only. It should be understood that various alternatives to the embodiments of the application described herein may be employed in practicing the application. Those ordinary skilled in the art will appreciate that numerous variations, changes, and substitutions are possible without departing from the application. It is intended that the following claims define the scope of aspects of the application and that methods and structures within the scope of these claims and their equivalents be covered thereby.

It is to be understood that, if any prior art publication is referred to herein, such reference does not constitute an admission that the publication forms a part of the common general knowledge in the art. All documents, or portions of documents, cited in the application including, without limitation, patents, patent applications, articles, books, manuals, and treatises are hereby expressly incorporated by reference in their entirety for any purpose.

The percentage herein is expressed by weight relative to the weight of the extract or the specified product, unless otherwise specified.

Further aspects and advantages of the invention will be disclosed in the following illustrative experimental section.

EXAMPLES

1. Preparation of Refined Indigo Naturalis Extracts and Analytical Methods for Analysis

Example 1

Preparation of a Refined Indigo Naturalis Extract

Qingdai as used in the following preparation is obtained from Delong Pharmaceutical (Indigo 2.62% and Indirubin 0.284% (HPLC method depicted in Example 7A) and tryptanthrin 0.0046% (HPLC method depicted in Example 8B)).

500 g of Qingdai were suspended in 10 L ethyl acetate. The mixture was stirred in reflux for two hours, and then filtered at 75° C. The filtrate was concentrated at reduced pressure to yield a dark solid. The crude extract was stirred in 250 mL hexane and heated to reflux for one hour. After cooling to room temperature, the suspension was filtered to give a dark residue.

0.50 g of the dark residue were refluxed in 25 mL hexane again for one hour, and cooled to room temperature, followed by filtration to give a refined extract as a dark red solid 452 mg. HPLC: 62.9% indirubin, 12.9% indigo, and 0.53% tryptanthrin.

Example 2

Preparation of a Refined Indigo Naturalis Extract 500 g of Qingdai as used in Example 1 were suspended in 10 L alcohol (ethanol). The mixture was stirred in reflux for two hours, and then filtered at 75° C. The filtrate was concentrated at reduced pressure to yield a dark solid, which was stirred in 260 mL hexane and heated to reflux for one hour. Upon cooling to room temperature, the suspension was filtered to give a dark residue.

0.80 g of the dark residue were refluxed in 24 mL alcohol (ethanol) for an additional hour, and then cooled to room temperature, followed by filtration to give a refined extract as a dark red solid (538 mg). HPLC: 83.6% indirubin, 6.35% indigo, and 0.75% tryptanthrin.

Example 3

Preparation of a Refined Indigo Naturalis Extract 500 g of Qingdai as used in Example 1 were suspended in 10 L ethyl acetate. The mixture was stirred in reflux for two hours, and then filtered while hot. The filtrate was concentrated at reduced pressure to yield a dark solid. The crude extract was stirred in 250 mL hexane and heated to reflux for one hour. After cooling to room temperature, the suspension was filtered to give a dark residue.

0.75 g of the dark residue were refluxed in 22.5 mL ethanol for one hour, and cooled to room temperature, followed by filtration to give a refined extract as a dark red solid (538 mg). HPLC: 77.9% indirubin, 15.9% indigo, and 0.56% tryptanthrin.

Example 4

Preparation of a Refined Indigo Naturalis Extract 500 g of Qingdai as used in Example 1 were suspended in 2.1 L DMF. The mixture was stirred at 50° C. for 40 minutes. Upon cooling to 20° C., the suspension was filtered. The filtrate was concentrated at reduced pressure to yield a dark solid, which was stirred in 130 mL hexane and heated to reflux for one hour. Upon cooling to 20° C., the suspension was filtered to give a dark residue.

1.56 g of the dark residue was washed with 46.8 ml ethanol, and heated to reflux for one hour, and then cooled to 20° C., followed by filtered to yield a refined extract (766 mg). HPLC: 66.3%, indirubin, 9.76% indigo.

Example 5

Preparation of a Refined Indigo Naturalis Extract 500 g of Qingdai as used in Example 1 were suspended in 3 L DMF. The mixture was stirred at 30° C. for 1 hour, and then filtered. The filtrate was concentrated at reduced pressure to yield a dark solid, which was stirred in 230 mL hexane and heated to reflux for one hour. Upon cooling to 20° C., the suspension was filtered to give a dark residue.

1.96 g of the dark residue was washed with 59 mL 85% ethanol (85% aq. alcohol), and heated to reflux for one hour followed by filtration while hot to yield a refined extract (1.02 g). HPLC: 69.4% indirubin, 18.7% indigo, and 0.62% tryptanthrin.

Example 6

Preparation of a Refined Indigo Naturalis Extract 100 g of Qingdai was extracted with 2 L of ethanol 92% (92% aqueous ethanol) for 2 hours under reflux conditions. Upon completion, the mixture was filtered while hot on AF6 filter (Buchner) to obtain a dark blue-red solution as a filtrate. This filtrate was reduced under vacuum to dryness to give 2.4 g of dry residue. This residue was washed with 120 mL of hexane for 1 h under reflux. Upon completion, the mixture was cooled to room temperature for 2 h then filtered under vacuum to yield 312.9 mg of a dark red refined extract.

280 mg of this refined extract were washed with 15 mL of ethanol 92% (92% aqueous ethanol) for 1 h under reflux. Upon completion the solution was cooled to room temperature, and then filtered to yield 159 mg of a dark red/burgundy refined extract after drying in oven (80° C.) for 1 h30. (0.18%); HPLC: 82.31% indirubin, 8.99% indigo, and 0.81% tryptanthrin.

Example 7

Micronization Step

The micronization step of refined Indigo Naturalis extract obtained in the previous examples is performed with the following equipment:

Micronizer: spiral jet Mill Diameter 200

Feeder: this equipment is used for the dosage of powder to feed the micronizer. The dosage is made thanks to two screws. This system allows a regularity of the flow.

Micronization consists to project grains of powder with jet of air. The contact of grains permits their explosion.

Following parameters of micronization are recorded during the micronization:

Ring pressure: 6 bar
Injector pressure: 3 bar
The flow of powder feed: 25 kg/h

The micronizer allows a cylindrical enclosure—holes around the enclosure for the injection of air.

Powder is introduced in the micronizer; grains are propelled thanks to jet of air. When grains have the good size, they are concentrated in the center of the micronizer and they are breathed. To avoid any contamination by foreign particles or broken pieces of the equipment, an additional sieving (sieve: 700 μm) is performed.

The step is done manually after the micronization and before the packaging.

A granulometric analysis of the homogeneous product obtained was carried out according to the particular size distribution (PSD) method [Analytical specifications: D99≤30 μm].

Example 8

Analytical Methods for Analysis

A—Reversed Phase HPLC Method:

A new reversed phase HPLC method to quantitate indigo and indirubin simultaneously was established based on European Pharmacopoeia (Pharmeuropa Vol. 20, No. 1, January 2008, P118-119.), Chinese Pharmacopoeia (2010 Edition, P185) and literatures (Chen L W, Liao W, Yang M. Jia D Y, He P, Chen S M, Fu C M. Determination of indigo and indirubin in Indigo Naturalis by HPLC. West China Journal of Pharmaceutical Sciences, 2008, 23(6), 714-715; Liu Z Y, Su Z T, Gao Y N, Yang M. Simultaneously determination of indigo and indirubin in Indigo Naturalis by HPLC. China Pharmacist 2010, 13(3), 324-326).

The chromatographic system (Agilent 1200 series) consisted of a G1322A degasser, a G1211A pump, a G1367B autosampler, a G1316A column oven and a G1315B DAD detector. Other apparatus included a SK7200H ultrasonic device (China) and a Milli-Q water purification system (USA).

Six batches of Qingdai were collected from three vendors in China. Indigo standard was purchased from Tokyo Chemical Industry Co. (Japan, >98%). Tryptanthrin was bought from Accela Co. (China, 97%). Indirubin was synthesized and recrystallized at Hutchison Medipharma (HMP) (>99% in HPLC).

Organic filter membrane (0.45 μm, China), Dimethyl formamide (DMF, analytical grade), methanol (HPLC grade), formic acid (FA, HPLC grade), triethylamine (TEA, analytical grade) and ultra-pure water purified with Milli-Q water purification system were used in the experiments.

Pretreatment of DMF solution: 500 mL of DMF was blown with dry N2 for half an hour, then 0.5 mL TEA was added and mixed to give a DMF solution (containing 0.1% TEA, free of oxygen). This DMF solution was used in sample preparation.

50 mg of Qingdai was suspended in 50 mL DMF solution. After ultrasonic extraction for 10 min, the suspension was filtered through 0.45 μm syringe filter to generate the test solution of Qingdai.

20 mg of Indigo Naturalis dried extract (obtained from Example 2) was suspended in 200 mL DMF solution. After ultrasonic extraction, the suspension was filtered through a 0.45 syringe filter to generate the test solution of Indigo Naturalis extract.

The separation was performed on a Waters Symmetry C18 column (5 μm, 3.9×150 mm). The mobile phase was 65% methanol (containing 0.05% FA). The flow rate was 1.0 mL/min for 15 min and the column temperature was 25° C. Injection volume was 4 μL. Detection wavelength was 289 nm so that indigo and indirubin could be assayed simultaneously. Indigo and indirubin could be analyzed simultaneously in one injection. Typical HPLC chromatograms of indigo and indirubin were shown in FIGS. 1A and 1B.

B—HPLC Analytical Method to Quantitate Tryptanthrin:

A new HPLC analytical method to quantitate tryptanthrin was also established. The sample concentration would be adjusted accordingly due to the low concentration of Tryptanthrin in both Qingdai and its enriched product, the dried extract. The analyses were performed at 25° C. on a Waters Symmetry C18 column (5 μm, 3.9×150 mm). The mobile phase was methanol (containing 0.05% FA, eluent B) and water (containing 0.05% FA, eluent A). The gradient elution profile was as follows: 50% B isocratic (12 min), 50% to 100% B (1 min), 100% B isocratic (6 min) and 100% to 50% B (1 min). The flow rate was 1.0 mL/min and the column temperature was 25° C. Injection volume was 10 μL. Detection wavelength was 254 nm.

400 mg of Qingdai was suspended in 20 mL DMF solution. After ultrasonic extraction for 20 min, the suspension was filtered through 0.45 μm syringe filter to provide the test solution of Qingdai.

15 mg of dried extract (obtained from Example 2) was suspended in 20 mL DMF solution. After ultrasonic extraction, the suspension was filtered through 0.45 μm syringe filter to provide the test solution of dried extract.

Figure 2A:
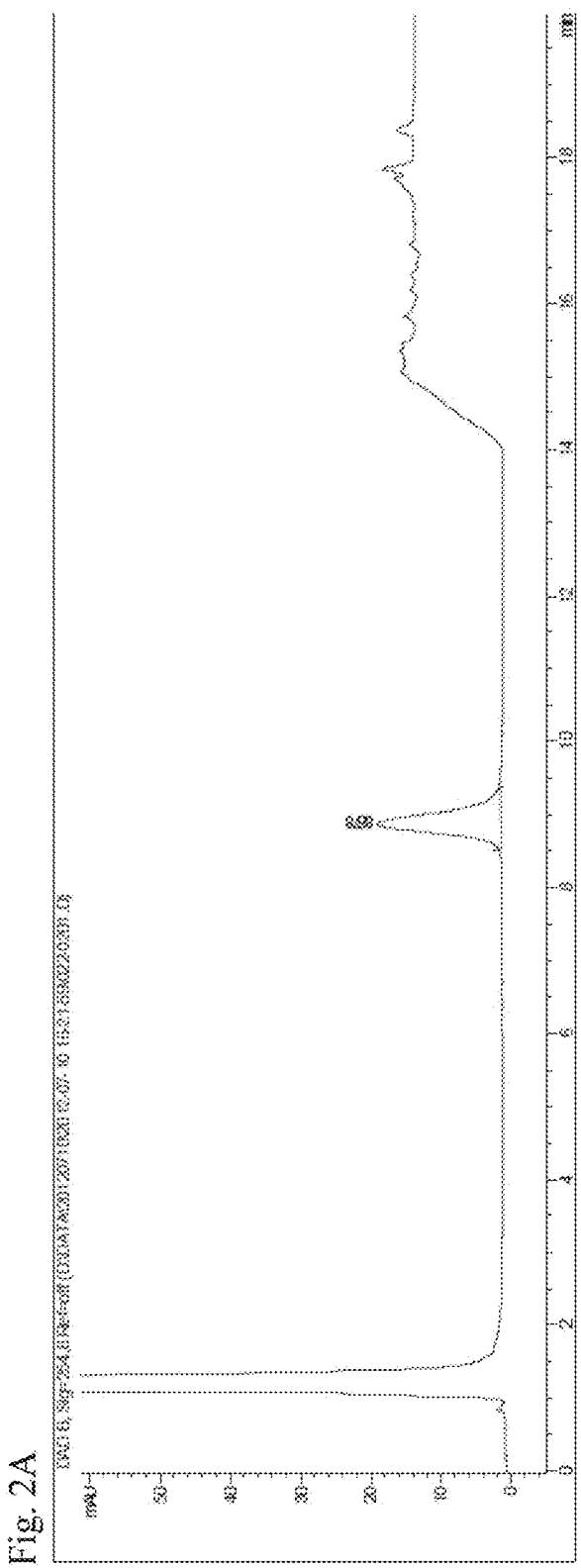
Figure 2C:
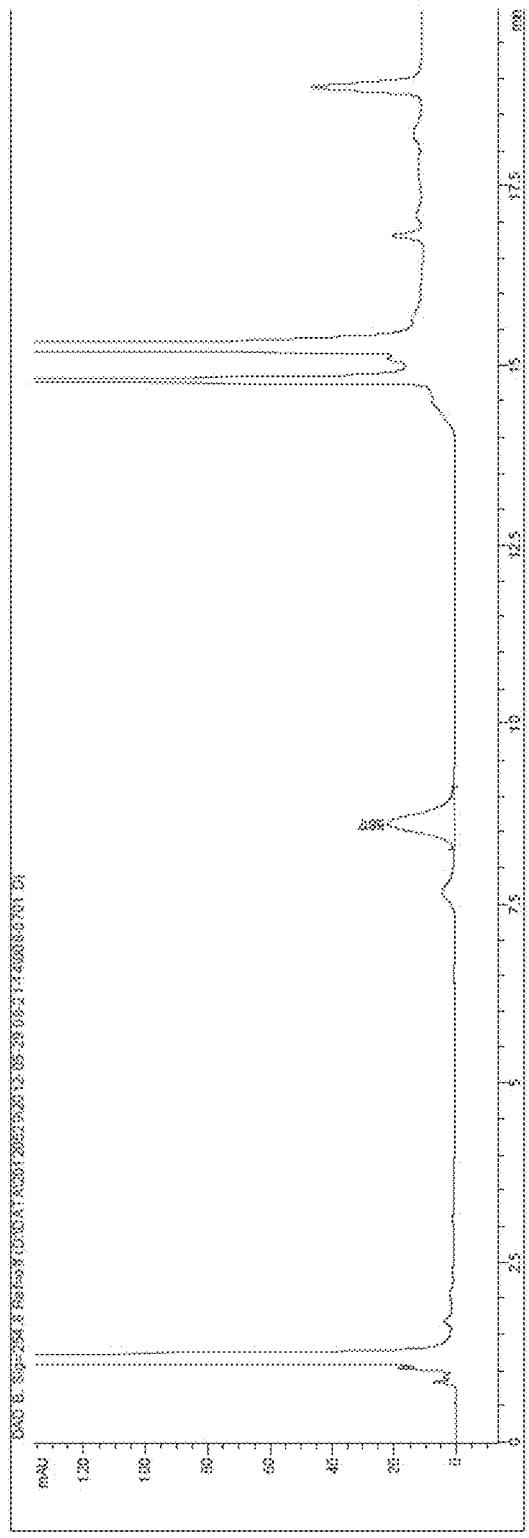

Typical HPLC chromatograms of thryptanthrin, Qingdai and a dried extract were shown in FIGS. 2A, 2B, and 2C.

2. In Vitro Evaluation of Refined Indigo Naturalis Extracts in Biochemical and Cellular Assays Example 9

In Vitro Assays and Results

A. General Reagents:
DMSO, Sigma-Aldrich, St. Louis, Mo., Cat. No. D2650
Janus kinase 1(JAK1), Life Technologies™, Cat. No. PV4774
Janus kinase 1(JAK2), Life Technologies™, Cat. No. PV4210
Janus kinase 1(JAK3), Life Technologies™, Cat. No. PV3855
CDK1, Life Technologies™, Cat. No. PV3292
CDK2, Life Technologies™, Cat. No. PV3267
CDK5, Life Technologies™, Cat. No. PV3000
Z'-LYTE® Kinase Assay Kit—Tyrosine 6 Peptide, Life Technologies™, Cat. No. PV4122
Z'-LYTE® Kinase Assay Kit—Ser/Thr 12 Peptide, Life Technologies™, Cat. No. PV3673
Dulbecco's modified Eagle's medium (DMEM), Life Technologies™, Cat. No. C11965
RMPI-1640, Life Technologies™, Cat. No. A10491
Fetal bovine serum (FBS), Life Technologies™, Cat. No. 10099141
EpiLife® Medium, Life Technologies™, Cat. No. M-EPI-500-CA
HKGS, Life Technologies™, Cat. No. S-001-5
Recombinant human IL-2, Peprotech Inc, Cat. No. 200-02
Recombinant human IL-6, Peprotech Inc, Cat. No. 200-06
Recombinant human IL-3, Peprotech Inc, Cat. No. 200-03
Recombinant human GM-CSF, Peprotech Inc, Cat. No. 300-03
Recombinant human IL-22, Peprotech Inc, Cat. No. 200-22
Recombinant human TNFα, R&D, Cat. No. 210-TA-010
Lipopolysaccharide (LPS), Calbiochem, Cat. No. 437650

Anti-Human CD3 Functional Grade® Purified (aCD3) (Clone: OKT3) eBioscience, Cat. No. 16-0037-85
Anti-Human CD28 Functional Grade® Purified (aCD28) (Clone: CD28.2), eBioscience, Cat. No. 16-02897-85
phospo-STAT3 (Y705) antibody (rabbit-anti-human), Cell Signaling Technology, Cat. No. 9145
phospo-STAT5 (Y694) antibody (rabbit-anti-human), Cell Signaling Technology, Cat. No. 9359
Actin antibody (mouse-anti-human) Sigma-Aldrich, Cat. No. A1978
Goat anti-rabbit IgGAlexa 488, Life Technologies™, Cat. No. A11034
Goat-anti-rabbit IROYE 800CW, Li-COR Bioscience, Cat. No. 926-32211
Goat-anti-mouse IROYE 800CW, Li-COR Bioscience, Cat. No. 926-32210
Human IFNγ ELISA Kit, R&D, Cat. No. DY285
Human TNFα ELISA Kit, R&D, Cat. No. DY210
Human IL-1β ELISA Kit, R&D, Cat. No. DY201
Human IL-6 ELISA Kit, R&D, Cat. No. DY206
Thiazolyl Blue Tetrazolium Blue (MTT), Sigma-Aldrich, Cat. No. M2128
CellTiter-Glo® Luminescent Cell Viability Assay, Promega, Cat. No. G7572
CytoTox-ONE™ Homogeneous Membrane Integrity Assay, Promega, Cat. No. G7891
Luciferase Assay, Promega, Cat. No. E4550
iBlot® Transfer Stack, Regular (Nitrocellulose), Life Technologies™, Cat. No. IB3010-01
Propidium iodide, Sigma-Aldrich, Cat. No. P4170
Ribonuclease A, Sigma-Aldrich, Cat. No. R6513
1×PBS Buffer (1 L): NaCl 8.0 g, KCl 0.2 g, $Na_2HPO_4$-$12H_2O$ 3.58 g, $KH_2PO_4$ 0.24 g, dissolved in 1 L MilliQ dd$H_2O$, pH adjusted to 7.4.
1×SDS loading buffer: 50 mMTris-HCl/pH8.8, 2% SDS, 10% glycerol, 0.1% bromophenol blue, 100 mM DTT.

B. Cell and Cell Lines

HepG2, a human hepatocellular carcinoma cell line, purchased from Shanghai Institutes for Biological Sciences (SIBS) (Shanghai, China, Cat. No. TCHu 72), were cultured in DMEM containing 10% FBS.
TF1, a human erythroleukemia cell line, purchased from American Tissue Culture Collection (ATCC) (Manassas, Va., Cat. No. CRL-2003™), were cultured in RMPI-1640 containing 10% FBS and 2 ng/mL of GM-CSF at 37° C. with 5% $CO_2$.
PBMCs: Normal human blood samples from healthy adult donors were collected in heparinized tubes. Each independent experiment used blood from a single healthy donor. Mononuclear cells (PBMCs) were isolated using Ficoll-Paque Plus reagent (Amersham Pharmacia Biotech, Sweden, Cat. No. 17-1440-02) according to protocol recommended by the manufacturer and cultured in RMPI-1640 containing 10% FBS at 37° C. with 5% $CO_2$.
Primary T cells: Mononuclear cells (PBMC) were isolated using Ficoll-Paque Plus reagent (Amersham Pharmacia Biotech, Sweden, Cat. No. 17-1440-02) according to protocol recommended by the manufacturer. Then cells were activated by using anti-CD3 (1 µg/mL) and anti-CD28 (5 µg/mL) for 3 days, and expanded in RMPI-1640 containing 10% FBS and long/mL IL-2 at 37° C. with 5% $CO_2$ every 2-3 days for 2 weeks prior to performing experiments.
HaCaT, a human epidermal keratinocyte line, was a kind gift from Prof. YuYiZhi (The Second Military Medical University (SMMU), China) and was cultured in DMEM containing 10% FBS.
HEKa, human epidermal keratinocytes isolated from adult skin, purchased from Life Technologies™ (Carlsbad, Calif., USA, Cat. No. C-005-5C) and cultured in EpiLife® Medium containing HKGS at 37° C. with 5% $CO_2$.
293/NFkB-Luc cell line was purchased from Panomics (Fremont, Calif., Cat. No. RC0014). It was obtained by co-transfection with pNFκB-Luc and pHyg into a human embryonic kidney 293 cells, followed by hygromycin selection. The cells were cultured in DMEM containing 10% FBS and 100 µg/mL hygromycin B (Life Technologies™, Cat. No. 10687-010).

C. Kinase Assay

JAK1/2/3 kinase assays were performed in vitro using recombinant human JAK1/2/3 and Z'-LYTE® Kinase Assay Kit—Tyrosine 6 Peptide. CDK1/2/5 kinase assays were performed in vitro using recombinant human CDK1/2/5 and Z'-LYTE® Kinase Assay Kit—Ser/Thr 12 Peptide. All reactions (20 µL) were started by adding 2.5 µL of positive control (CP-690550 for JAK kinase assay and Staurosporine for CDK kinase assay) or the test articles (i.e., samples) in 4% DMSO solution, 5 µL of Kinase/Peptide substrate Mixture or Phospho-Peptide solution, 2.5 µL ATP Solution (100 µM) or 1.33×Kinase Buffer. The 384-well assay plate (Corning, Cat. No. 3575) was mixed and incubated at room temperature for 1 hour. 5 µL of the Development Solution was then added to each well, mixed and incubated at room temperature for another 1 hour. The kinase reactions were then stopped by adding 5 µL of the Stop Reagent followed by recording 450 nm and 520 nm fluorescence's using Perkin-Elmer Victor III (Perkin-Elmer Life Sciences, Boston, Mass.) plate reader.

D. Acumen Assay

For IL-6 induced STAT3 phosphorylation, HepG2 were seeded in 96 well plates at $5.4×10^3$ cells per well in serum-free DMEM media at 37° C., 5% $CO_2$ overnight. After incubation with CP-690550 or test articles for 30 minutes, cells were stimulated by adding 100 ng/mL human recombinant IL-6 (1:10) to each well for 15 minutes.

For IL-3 induced STAT5 phosphorylation, TF-1 was seeded in 96-well plates at $1×10^4$ cells per well at 37° C., 5% $CO_2$ for 3 hours. After incubation with CP-690550 or test articles for 30 minutes, cells were stimulated by adding 100 ng/mL human recombinant IL-3(1:10) to each well for 30 minutes.

HepG2 or TF1 cells were then fixed in 2% paraformaldehyde for 45 minutes at room temperature and incubated in ice-cold methanol for 30 minutes. After washing with PBS, cells were incubated with anti-phospho-STAT3 (Y705) or anti-phospho-STAT5 (Y694) antibody respectively at 4° C. overnight. Goat anti-rabbit IgG Alexa 488 secondary antibody was added for 90 minutes prior to PBS washes. Cells were counted following incubation in PBS containing 7.5 µM Propidium iodide and 100 µg/mL Ribonuclease A for 60 minutes in the dark. Plate was read on an Acumen X3 instrument (TPP Labtech, Hertfordshire SG8, UK).

E. Western Blots

HEKa were seeded in 6-well plates at $2×10^5$ cells/well at 37° C., 5% $CO_2$ overnight. After incubation with test article for 30 minutes, the cells were stimulated with 100 ng/mL IL-22 for 30 minutes.

After the treatment, samples were collected in 1×SDS loading buffer. Protein samples were boiled for 15 minutes and collected by centrifugation at 14,000 g for 10 min at 4° C. The supernatants were used or immediately stored at −80° C. For Western blot analysis, samples were separated on a 10% Tris-HCL gradient electrophoresis gel (Bio-Rad Laboratories). Gels were blotted onto a iBlot® Transfer Stack, Regular (Nitrocellulose) which was blocked in 5% nonfat dry milk and probed using anti-phospho-STAT3 (Y705) antibody or anti-Actin antibody at 4° C. overnight, respectively. The membrane was then incubated with appropriate IDRye 800CW secondary antibody followed by detection using Odyssey infrared imaging System (Li-COR Bioscience, Lincoln, Nebr., USA).

F. Reporter Assays

For reporter gene assays, the 293/NFκB-Luc was seeded in 96-well plate at $4 \times 10^4$ cells per well overnight. After the incubation with Andrographolide (LGT) or test articles for 30 minutes, cells were stimulated by adding 100 ng/mL TNFα (1:10) to each well for 6 hours. Cell lysates were prepared by removing media and adding lysis buffer. 5× volume Luciferase Assay Reagent was added to each well prior to read plate. Luminescence was recorded using Perkin-Elmer Victor III plate reader (Perkin-ElmerLife Sciences, Boston, Mass., USA).

G. ELISA Assay

Primary T cells were seeded in 96-well plates at $8 \times 10^4$ cells/well. Test articles were added into the cultures and incubated at 37° C., 5% $CO_2$. After 30 minutes, the cell suspension in each well was transferred to another 96-well plate coated with a CD3 (1 μg/mL) and a CD28 (5 μg/mL) and incubated at 37° C. with 5% $CO_2$ for 22 hours. The media were removed and stored at −80° C. until assayed. IFNγ concentrations were determined using a commercial ELISA kit (R & D Systems), following the manufacturer's instruction.

PBMCs were seeded in 96-well plates at $3 \times 10^4$ cells per well. Test articles were then added into the culture and incubated at 37° C., 5% $CO_2$. After 30 minutes, 1 μg/mL LPS (1:10) was added to the culture. For quantitation of protein levels, the plates were incubated for 18 hours. The media were removed and stored at −80° C. until assayed. TNFα, IL-1β and IL-6 concentrations were determined using commercial ELISA kits (R & D Systems), following the manufacturer's instructions.

H. MTT Assay

HaCaT were seeded in 96-well plates at $4 \times 10^4$ cells/well overnight. Stausporine or test articles were then added into the culture and incubated at 37° C., 5% $CO_2$ for 72 hours. After removal of the media, the cells in 96-well plates were exposed to 100 μL of MTT (0.5 mg/mL in DMEM containing 10% FBS per well and incubated for 3 hours at 37° C., 5% $CO_2$. Subsequently, the supernatants were removed and 150 μL of DMSO were added to each well. The plate was incubated in the dark for 10 minutes and the absorbance at 492 nm was recorded immediately using Multiskan MK3microplate reader (Thermo Life Sciences, HK, China).

I. Cell Viability Assay

CellTiter-Glo® Luminescent Cell Viability Assay. Kit was used to investigate cell viability. HEKa were seeded in 96-well opaque-walled plate at $1 \times 10^4$ cells/well overnight. Dithranol or test articles were then added into the culture and incubated at 37° C., 5% $CO_2$ for 48 hours. Cells were lysed with CellTiter-Glo® Reagent equal to the volume of cell culture media present in each well, and contents mixed for 2 minutes to induce cell lysis. Plate was incubated at room temperature for 10 minutes to stabilize luminescent signal. Luminescence was recorded using Perkin-ElmerVictor III plate reader (Perkin-Elmer Life Sciences, Boston, MA, USA).

J. LDH Release Assay

Lactate dehydrogenase (LDH) release assay kit was used to investigate cytotoxicity. HEKa were seeded in 96-well opaque-walled plates at $4 \times 10^4$ cells/well overnight. Dithranol or test articles were then added into the culture and incubated at 37° C. under 5% $CO_2$ for 24 hours. Supernatants and cell lysates were prepared. 1× volume of CytoTox-ONE™ Reagent equal to the volume of supernatants or cell lysates were added to each well followed by mixing for 30 seconds and incubating at 25° C. for 10 minutes. Stop solution equal to 50% volume of the supernatants or cell lysates were added to each well to stop the reaction, and fluorescence with an excitation wavelength of 560 nm and an emission wavelength of 590 nm were recorded using SpectraMax M2 (Molecular Devices, Sunnyvale, Calif., USA).

K. TNFα-Induced NFκB Activation (hmp 2.3.2.1, Table 22)

Pro-inflammatory cytokines and chemokines play important roles in pathogenesis of psoriasis. NFκB is clearly one of the most important regulators of pro-inflammatory cytokine and chemokine gene expression. Therefore, inhibitory potency of Qing Dai and its refined extracts on TNFα-dependent NFκB activation was investigated in HEK 293/NFκB-Luc. As shown in Table 1, TNFα stimulated NFκB-dependent luciferase expression and pretreating cells with Tripterygium Glycoside blocked NFκB activation in a concentration dependent manner. Indigo Naturalis refined extract had microgram/g activities on TNFα-dependent NFκB activation on the experimental condition. (see Table 1)

L. $IC_{50}$ Determinations

All IC50 values were determined by using Xlfit™ software (version 2.0) from ID Business Solutions (Guildford, UK). Background was defined in culture with cells treated with DMSO only and was subtracted for $IC_{50}$ calculations.

M. Results

Some in vitro assay results of some of Indigo Naturalis refined extracts are shown in Table 1 below, wherein Indigo Naturalis A is obtained from Delong Pharmaceutical: (Indigo 2.62%, Indirubin 0.284%; Tryptanthrin 0.0046%).

TABLE 1

| Sample | pro-inflammatory cytokine production $IC_{50}$ (NFκB) μg/mL | HaCaT proliferation $IC_{50}$ μg/mL | HEKa Viability $IC_{50}$ μg/mL |
| --- | --- | --- | --- |
| Staurosporine | | 3.18(nM) +/− 2.19 | |
| LGT | 0.00045 | | |
| Indigo Naturalis A** | | 2.42/2.43 | |
| Example 4 | 10.87/63.53/ 10.37/25.75 | 1.57/<0.82/1.02 | |
| Example 1 | 8.47/15.40 | | 2.91 ± 0.49 (n = 2) |
| Example 3 | 37.23/>100 | | 1.71 ± 0.54 (n = 3) |
| Example 2 | 51.03/41.79 | | 1.75 ± 0.48 (n = 4) |

TABLE 1-continued

| Sample | pro-inflammatory cytokine production IC$_{50}$ (NFκB) µg/mL | HaCaT proliferation IC$_{50}$ µg/mL | HEKa Viability IC$_{50}$ µg/mL |
|---|---|---|---|
| Example 5 | 24.66/32.97 | | 2.21 ± 0.45 (n = 4) |

**Indigo Naturalis A: Indigo Naturalis from Delong Pharmaceutical: Indigo 2.62%, Indirubin 0.284%; Tryptanthrin 0.0046%

3. In Vivo Evaluation of Refined Indigo Naturalis Extracts in Animal Models

Example 10

In Vivo Assays and Results

A. Materials and Methods
Animals
BABL/c mice, male, body weight 19~22 g, purchased from Shanghai SLC AnimalCenter.
Room temperature: 24±1° C.
Room relative humidity: 40-70%
Light cycle: Fluorescent light for 12-hour light (8:00-20:00) 12-hour dark
Animal hosting: 4 mice/cage
Food: Free access to food (irradiated, Shanghai SLAC Laboratory Animal Co. Ltd., China)
Water: Free access to tap water from local supply (first filtered by Molanimal ultrapure water machine from the municipal water supply)
Instruments
MJ Research PTC-200 Peltier Thermal cycler (Alpha Unit™ Block Assembly for PTC DNA Engine™ systems)
Applied Biosystems 7500 realtime PCR system
Digimatic micrometer caliper: Mitutoyo, Japan. Accuracy: 0.001 mm
Reagents
Recombinant mouse IL-22 (rmIL-22), Novoprotein (sinobio), Cat. C047, Lot. 0375351 High capacity cDNA Reverse Transcription kit, Applied Biosystems, Part No.: 4368813, Lot: 0909069
Thermo Scientific ABsolute SYBR Green Rox Mix, Thermo Scientific, Cat: AB-1163/A, Lot: 0911/16
Positive Control
Protopic® (tacrolimus, FK506), 0.1% ointment, Astellas Toyama Co., Ltd. Toyama Plant, H 20100079, Lot: 028680.
Dosing Regimen
   Different concentrations of test samples, vehicle, or 0.1% of FK506 ointment, were topically administrated at 1% one hour after the induction of model and then given daily from day 1 to day 11, twice a day. The first day of administration of a test article was regarded as day 0.
Route of Administration
   Topical Application, b.i.d.
Establishment of IL-22 Induced Psoriasis-Like Mouse Models
   Intradermal injection of 20 µL PBS, either alone or containing 100 or 500 ng recombinant mouse IL-22 (eBiosience), was administered into the ears of anesthetized mice using a 30-gauge needle every other day for eleven days. Ear thicknesses were measured before injection on day 0 and thereafter on days without injections. Ear measurements were taken at the center of the ears using a digimatic micrometer caliper (Mitutoyo).

Twenty-four hours after the last IL-22 treatment, mice were sacrificed, and ears were collected for further analysis.
Histological Examination
   Ears were collected at necropsy, fixed in 10% buffered formalin phosphate, embedded in paraffin, sectioned, and stained with hematoxylin/eosin (H&E). Microscopic sections were graded by the number and severity of lesions.
Statistical Methods
   Results of ear thickness data were expressed as mean±S.E.M. AUC of ear swelling was calculated by the ear thickness data from day 0 to day 11, and analyzed by repeated-measured ANOVA methods with JMP® software. Cytokine protein and gene expression data were evaluated with a one-way ANOVA and followed by student's t-test for post-hoc analysis. (Significance level was set at p<0.05).
Group and Dosing
   See FIGS. 3A, 3B, 3C, 3D, and 3E.
Results
   Some in vivo assay results of some of Indigo Naturalis refined extracts are shown in Table 2.

TABLE 2

Figure 4A:
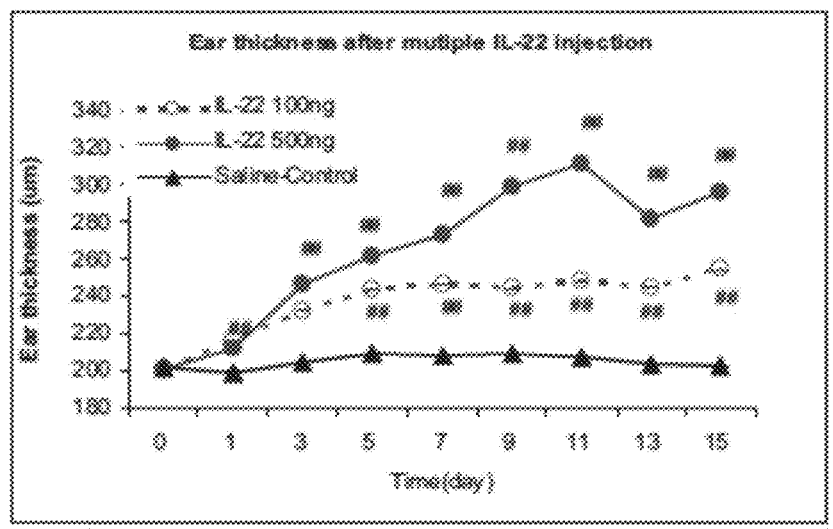
FIGS. 4A, 4B.
Figure 4B:
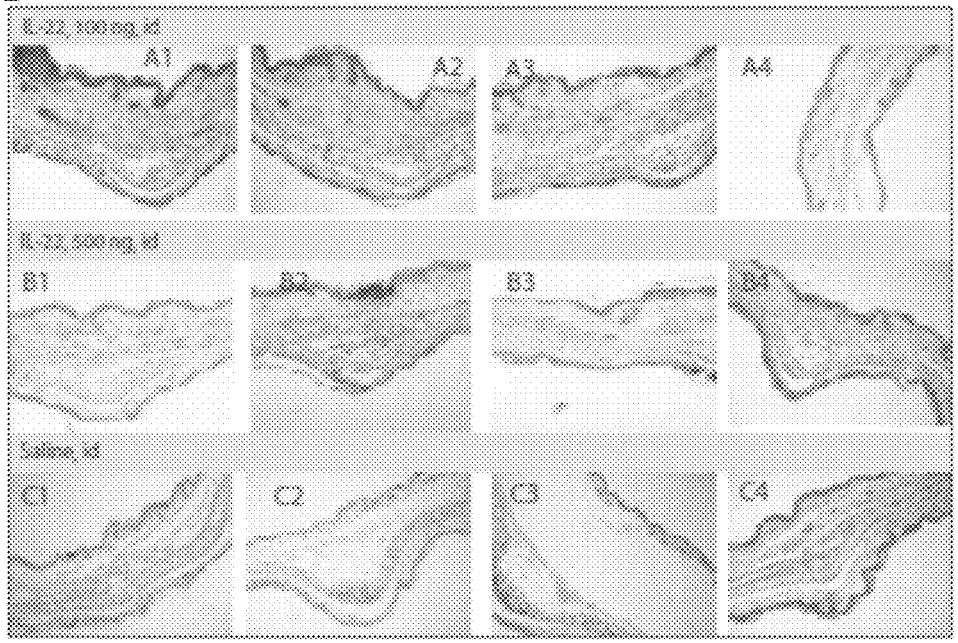
Figure 5A:
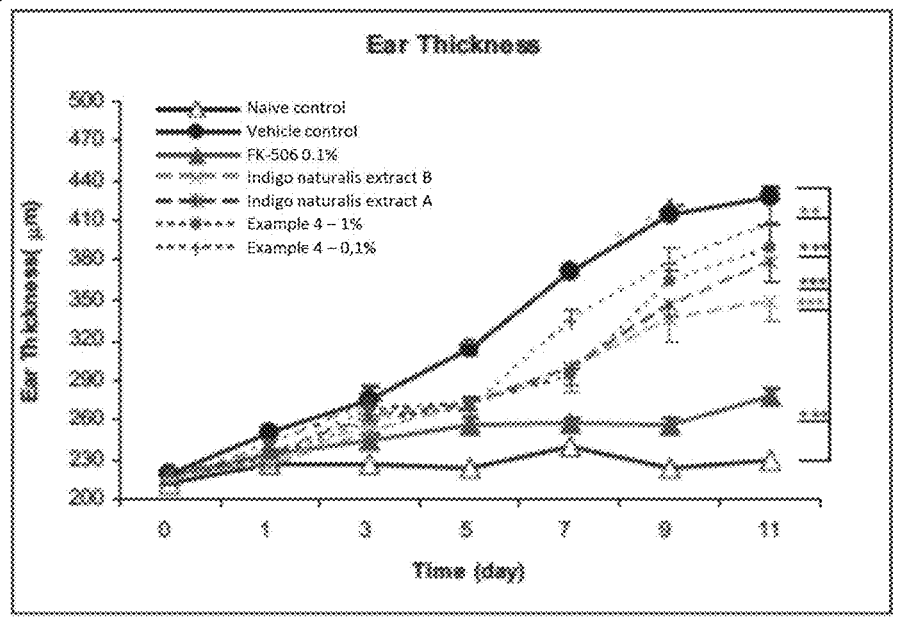
FIGS. 5A, 5B.

| In vivo studies | group | ear thickness on day 11 (µm) | AUC of ear thickness | inhibition of AUC of ear thickness (%) |
|---|---|---|---|---|
| study 1 (cf FIGS. 4A and 4B) | saline-control (naïve) | 207.8 ± 1.8, 202.8 ± 2.2 (d15) | 61 | |
| | IL-22, 100 ng | 248.3 ± 1.9, 255.3 ± 15.1 (d15) | 590 | |
| | IL-22, 500 ng | 311.3 ± 18.0, 296.3 ± 5.0 | 1055 | |
| study 2 | naïve control | 236.7 ± 2.8 | 172 | |
| | vehicle 1 control | 371.3 ± 8.7 | 1281 | |
| | FK506 (0.1%) | 256.8 ± 3.5 | 403 | 79.2 |
| | Indigo Naturalis B* (10%) | 328.8 ± 16.8 | 749 | 48 |
| study 3 (cf FIG. 5A) | naïve control | 230.2 ± 4.4 | 165 | |
| | vehicle control | 428.3 ± 6.6 | 1256 | |
| | FK506 (0.1%) | 278.8 ± 5.0 | 369 | 81.3 |
| | Indigo Naturalis B*(10%) | 349.3 ± 14.6 | 703 | 50.7 |
| | Example 4 (1%) | 289.3 ± 17.4 | 876 | 34.8 |
| | Example 4 (0.1%) | 408.7 ± 18.0 | 975 | 25.7 |
| study 4 | naïve control | 233.1 ± 3.6 | 238 | |
| | vehicle control | 356.4 ± 11.8 | 1301 | |
| | FK506 (0.1%) | 260.4 ± 4.5 | 446 | 80.4 |
| | Example 4 (0.5%) | 310.4 ± 4.4 | 969 | 31.3 |
| | Example 4 (0.1%) | 303.8 ± 4.3 | 868 | 40.7 |
| | Example 4 (0.02%) | 302.8 ± 6.4 | 922 | 35.7 |

TABLE 2-continued

Figure 5B:
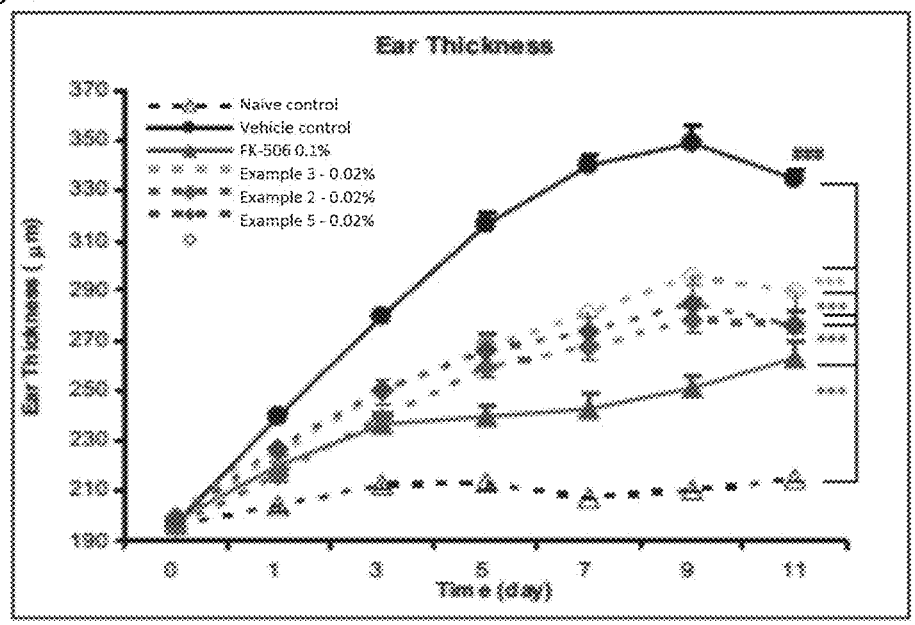

| In vivo studies | group | ear thickness on day 11 (μm) | AUC of ear thickness | inhibition of AUC of ear thickness (%) |
|---|---|---|---|---|
| study 5 (cf FIG. 5B) | naïve control | 214.5 ± 1.1 | 143 | |
| | vehicle control | 334.3 ± 3.3 | 1194 | |
| | FK506 (0.1%) | 263.4 ± 6.3 | 454 | 70.4 |
| | Example 3 (0.02%) | 289.6 ± 8.0 | 751 | 42.2 |
| | Example 2 (0.02%) | 276.3 ± 3.2 | 627 | 53.9 |
| | Example 5 (0.02%) | 275.5 ± 5.9 | 677 | 49.2 |

*Indigo Naturalis B: Indigo Naturalis from Qingfeng Pharmaceutical: Indigo 2.02%, Indirubin 0.216%; Tryptanthrin 0.0032%

4. Preparation of a Pharmaceutical Composition Containing a Refined Indigo Naturalis Extract.

Example 11

Formulation a (Indigo Naturalis Ointment)

| Phase | Composition | % w/w |
|---|---|---|
| A | Olea Europaea fruit oil (olive oil) | 81.873 |
| A | Butylated hydroxytoluene (BHT) | 0.10 |
| A | Refined Indigo Naturalis extract prepared according to example 6* | 0.027 |
| B | Beeswax, (white) | 9 |
| B | White Petrolatum | 9 |

*HPLC: 79.26% indirubin, 6.15% indigo, and 0.62% tryptanthrin.

Manufacturing Process:

Step 1: Refined Indigo Naturalis extract, olive oil and BHT have been stirred and heated at 90° C. for at least 20 minutes in order to obtain a homogeneous preparation. This mixture constituted phase A.

Step 2: Beeswax (white) and white petrolatum have been added to Phase A at 90° C. and stirred at least 20 minutes until the mixture was homogeneous.

Step 3: The homogeneous mixture from step 2 has been cooled to 55° C. while stirring.

Step 4: The contents of step 3 have been maintained at 55° C. and the finished product has been filled into the packaging.

Initial (T=0) Specifications:

Macroscopic aspect: homogeneous and viscous fushia colored ointment

Physical Stability:

| | Time | | |
|---|---|---|---|
| Storage conditions | T 1 Month | T 2 Months | T 3 Months |
| RT (Room Temperature) | Complies with initial (T = 0) specification | | |
| 30° C. | Complies with initial (T = 0) specifications | | |
| 40° C. | Complies with initial (T = 0) specifications | | |

Chemical Stability:

The chemical stability of Indigo Naturalis Ointment has been evaluated by chemical assay of indirubine.

Indirubin is assayed in Indigo Naturalis Ointment using reverse phase high performance liquid chromatography (HPLC) and results are expressed as mg/g of indirubine in Indigo Naturalis Ointment.

| | Time | | | |
|---|---|---|---|---|
| Storage conditions | T0 | T 1 Month | T 2 Months | T 3 Months |
| | Indirubine (mg/g of ointment) | | | |
| 25° C. | 0.206 | 0.205 | 0.205 | 0.210 |
| 30° C. | — | 0.207 | 0.205 | 0.209 |
| 40° C. | — | 0.205 | 0.206 | 0.211 |

The results showed that the Indigo Naturalis ointment was physically and chemically stable for 3 months at RT, 30° C. and 40° C.

Chemical stability is defined as an assay value of ≥90% of T0 values.

Physical stability is defined as no significant change from initial observations.

Example 12

Formulation B

| Phase | Composition | % w/w |
|---|---|---|
| A | Caprylic/Capric Triglyceride | 69.973 |
| A | Refined Indigo Naturalis extract prepared according to example 6* | 0.027 |
| A | Glyceryl Dibehenate (and) Tribehenin (and) glyceryl behenate | 6 |
| A | Hydrogenated castor oil | 3 |
| A | Glyceryl stearate | 6 |
| B | PPG-15 stearyl ether | 15 |

*HPLC: 79.26% indirubin, 6.15% indigo, and 0.62% tryptanthrin.

Manufacturing Process:

Step 1: Refined Indigo Naturalis extract has been added to caprylic/capric triglyceride and has been heated to 90° C. and mixed for at least 20 minutes in order to obtain a homogeneous preparation.

Step 2: Glyceryl dibehenate (and) tribehenin (and) glyceryl behenate, hydrogenated castor oil, and glyceryl stearate have been added to the contents of step 1. The mixture has been maintained at 90° C. and has been stirred for at least 10 minutes until homogeneous.

Step 3: The contents of step 2 (Phase A) has been cooled to 55° C. while stirring.

Step 4: Phase B (PPG-15 stearyl ether) has been added to Phase A at 55° C. while stirring for at least 10 minutes at 55° C. until homogeneous.

Step 5: Contents of step 4 have been cooled while stirring until the mixture reaches room temperature.

5. In Vitro Percutaneous Absorption in Ointment Formulations According to Example 11 (Formulation A).

This study compares the skin absorption and distribution of indirubin formulated in two different ointments containing Indigo Naturalis extract in ex vivo human skin.

One ointment (ointment 1) is disclosed at example 11 of the present invention (Formulation A) and the other ointment (ointment 2) has been prepared according to prior art US 2012/213868 with an Indigo Naturalis extract prepared also according to US 2012/213868 (Formulation C).

The two ointment formulations are illustrated in the following table 3.

TABLE 3

| Ingredients (%) | Ointment 1 (Formulation A) | Ointment 2 (Formulation C) |
| --- | --- | --- |
| Refined Indigo Naturalis Extract (Example 6) | 0.027 | — |
| Indigo Naturalis Extract (according to US 2012/213868) | — | 0.02 |
| Olive oil | — | 83.28 |
| Refined olive oil | 81.873 | — |
| BHT (antioxidant) | 0.1 | — |
| Bees wax | 9 | 16.7 |
| Petrolatum | 9 | 0 |

Experimental Procedures

In vitro absorption studies were conducted using split-thickness human skin (thickness ranged between 0.59 and 0.91 mm) mounted on diffusion cells. Each condition was tested in four replicates over four different donors, giving a total of 16 values per condition.

A dose of 10 mg/cm$^2$ of each formulation was applied on the skin surface with an application area of 2 cm$^2$ and a receptor compartment filled with 3 mL of phosphate buffer saline containing 0.1% (v/v) Tween-80. The test system was thermostated with a water circulating bath set at 37° C. and the receptor liquid was continuously stirred at 350 rpm. Treatment duration was 24 hours under static conditions and inactinic light.

Concentrations of indirubin were measured in epidermis including stratum corneum, dermis, receptor liquid and formulation excess samples using an LC-MS/MS method. The limit of quantification was 0.05 ng/mL in all matrices.

Results

The results of indirubin release in skin compartments are presented in Table 4 and showed that the mass balances of indirubin represented 102% and 105% of the indirubin applied dose for the ointment 1 and for the ointment 2, respectively.

Whatever the formulation applied, indirubin was distributed in the epidermis (including stratum corneum) the dermis and the receptor liquid.

TABLE 4

Release of Indirubin in split thickness human skin after a 24-hour treatment period (Arithmetic mean and SEM; N = 16)

| | | Ointment 1 (Formulation A) | Ointment 2 (Formulation C) |
| --- | --- | --- | --- |
| Epidermis + Stratum corneum | ng/cm$^2$ | 34.33 (3.05) | 27.89 (2.88) |
| | % of the applied dose | 1.60 (0.15) | 1.51 (0.16) |
| Dermis | ng/cm$^2$ | 20.04 (2.06) | 11.67 (1.41) |
| | % of the applied dose | 0.93 (0.11) | 0.63 (0.08) |
| Receptor liquid | ng/cm$^2$ | 6.16 (0.66) | 3.28 (0.34) |
| | % of the applied dose | 0.29 (0.03) | 0.18 (0.02) |
| Total penetrated | ng/cm$^2$ | 60.53 (4.89) | 42.83 (4.18) |
| | % of the applied dose | 2.82 (0.26) | 2.32 (0.23) |
| Mass balance | ng/cm$^2$ | 2192.85 (58.76) | 1933.90 (84.57) |
| | % of the applied dose | 102.10 (1.49) | 104.57 (4.19) |
| Ratio of geometric means obtained from statistical analysis | Using results of total penetrated expressed in ng/cm$^2$ | 148.78 | |
| | Using results of total penetrated expressed in ng/cm$^2$ | 125.12 | |

Total penetrated: Sum of the amounts recovered in epidermis + stratum corneum; dermis and receptor liquid
Values in brackets correspond to SEM values.
*Ratio of geometric means "Test group over Reference group" with Test group being the ointment 1 and Reference group being the ointment 2.

With ointment 1, indirubin represented 1.60%, 0.93% and 0.29% of the indirubin applied dose in epidermis (stratum corneum included), dermis, and receptor liquid, respectively. The total penetrated of indirubin represented 2.82% of the indirubin applied dose.

With ointment 2, indirubin represented 1.51%, 0.63% and 0.18% of the indirubin applied dose in epidermis (stratum corneum included), dermis, and receptor liquid, respectively. The total penetrated of indirubin represented 2.32% of the indirubin applied dose.

Statistical analyses using bioequivalence approach have been performed and the geometric mean ratios obtained for the total penetrated are presented in Table 4 above. Both geometric mean ratios were outside the acceptance interval [80.00%-125.00%] thereby showing a higher indirubin skin absorption for the ointment 1 compared to the ointment 2 (49% more indirubin delivered by ointment 1 based on analysis of total penetrated expressed in ng/cm$^2$: see table 5 below).

TABLE 5

Analysis done on results expressed in ng/cm$^2$

| Analysis | Geometric mean ratio Test/Reference (%)* | Acceptance interval | Result | Comparison |
| --- | --- | --- | --- | --- |
| Epidermis + SC | 126.90 | [80.00%-125.00%] | >125% | Different |
| Dermis | 174.77 | [80.00%-125.00%] | >125% | Different |
| Receptor liquid | 188.64 | [80.00%-125.00%] | >125% | Different |
| Total penetrated | 148.78 | [80.00%-125.00%] | >125% | Different |

*Test = Ointment 1
Reference = Ointment 2

In conclusion the inventors have surprisingly demonstrated that indirubin was distributed in epidermis (stratum corneum included), dermis and receptor liquid (see table 4) and that skin absorption of indirubin was significantly higher with a formulation of the invention compared to the formulation according to US 2012/213868.

The invention claimed is:

1. A solid extract of Indigo Naturalis comprising, relative to the total weight of the extract:
   65% to 90% (w/w) indirubin;
   0.1-15% (w/w) indigo; and
   0.01-5% (w/w) tryptanthrin.

2. The solid extract of claim 1, comprising 0.1-5% (w/w) tryptanthrin relative to the total weight of the extract.

3. The solid extract of claim 2, further comprising 0.1-5% (w/w) qingdainone relative to the total weight of the extract.

4. The solid extract of claim 3, being micronized and comprising particles having a particle size of less than or equal to 30 μm in 99% of the particles.

5. A pharmaceutical composition comprising a solid extract of Indigo Naturalis and a pharmaceutically acceptable carrier, wherein the solid extract comprises, relative to the total weight of the extract:
   65% to 90% (w/w) indirubin;
   0.1-15% (w/w) indigo; and
   0.01-5% (w/w) tryptanthrin.

6. The pharmaceutical composition of claim 5, comprising 0.002% to 0.077% (w/w) of the solid extract relative to the total weight of the pharmaceutical composition, and a pharmaceutically acceptable carrier comprising at least one of an oil, an emulsifier, a thickening agent, and a preservative.

7. The pharmaceutical composition of claim 6, wherein the solid extract comprises 0.1-5% (w/w) tryptanthrin relative to the total weight of the extract.

8. The pharmaceutical composition of claim 7, wherein the solid extract further comprises 0.1-5% (w/w) qingdainone relative to the total weight of the extract.

9. The pharmaceutical composition of claim 8, wherein the solid extract is micronized and comprises particles having a particle size of less than or equal to 30 μm in 99% of the particles.

10. The pharmaceutical composition of claim 5, wherein the composition is in the form for topical administration or oral administration.

11. A topical pharmaceutical composition comprising a micronized solid extract of Indigo Naturalis and a pharmaceutically acceptable carrier, wherein the solid extract comprises, relative to the total weight of the extract:
    65% to 90% (w/w) indirubin;
    0.1-15% (w/w) indigo; and
    0.01-5% (w/w) tryptanthrin.

12. The topical pharmaceutical composition of claim 11, comprising 0.002% to 0.077% (w/w) of the solid extract relative to the total weight of the pharmaceutical composition, and a pharmaceutically acceptable carrier comprising at least one of an oil, an antioxidant, an emulsifier, a thickening agent, and a preservative.

13. The topical pharmaceutical composition of claim 12, wherein the solid extract comprises 0.1-5% (w/w) tryptanthrin relative to the total weight of the extract.

14. The topical pharmaceutical composition of claim 13, wherein the solid extract further comprises 0.1-5% (w/w) qingdainone relative to the total weight of the extract.

15. The topical pharmaceutical composition of claim 14, wherein the solid extract comprises particles having a particle size of less than or equal to 30 μm in 99% of the particles.

16. A method of treating a disease or condition selected from the group consisting of psoriasis, an inflammatory skin condition, onychomycosis, skin cancer, abnormal keratinization induced diseases, skin aging, pustular dermatosis, comprising administering to a subject in need thereof a pharmaceutical composition of claim 5.

17. A method of treating a disease or condition selected from the group consisting of psoriasis, an inflammatory skin condition, onychomycosis, skin cancer, abnormal keratinization induced diseases, skin aging, pustular dermatosis, comprising topically administering to a subject in need thereof a pharmaceutical composition of claim 11.

18. The method of claim 17, wherein the disease or condition is psoriasis, an inflammatory skin condition, onychomycosis, skin aging or pustular dermatosis.

19. The method of claim 18, wherein the disease or condition is the inflammatory skin condition selected from the group consisting of atopic dermatitis (AD), eczema and superinfected skin.

20. The method of claim 17, wherein the disease or condition is the abnormal keratinization induced disease selected from the group consisting of acne, ichtyosis and palmoplantar keratoderma.

* * * * *